US012661139B1

(12) United States Patent
Voic et al.

(10) Patent No.: US 12,661,139 B1
(45) Date of Patent: Jun. 23, 2026

(54) SHEATHS FOR ULTRASONIC SURGICAL DEVICES, AND SYSTEMS, COMPONENTS, AND METHODS THEREOF

(71) Applicant: Misonix, LLC, Farmingdale, NY (US)

(72) Inventors: Dan M. Voic, Cedar Grove, NJ (US); Scott S. Isola, Deer Park, NY (US)

(73) Assignee: Misonix, LLC, Farmingdale, NY (US)

( * ) Notice: Subject to any disclaimer, the term of this patent is extended or adjusted under 35 U.S.C. 154(b) by 0 days.

(21) Appl. No.: 19/320,868

(22) Filed: Sep. 5, 2025

(51) Int. Cl.
*A61B 17/32* (2006.01)

(52) U.S. Cl.
CPC ............................ *A61B 17/320068* (2013.01)

(58) Field of Classification Search
CPC ........... A61B 17/320068; A61B 2017/320069;
A61B 2017/320071; A61B 2017/320072;
A61B 2017/320073; A61B 2017/320074;
A61B 2017/320075; A61B 2017/320078;
A61B 2017/320082; A61B 2017/320088;
A61B 2018/00577; A61F 9/00745
See application file for complete search history.

(56) References Cited

U.S. PATENT DOCUMENTS

| | | | |
|---|---|---|---|
| 5,221,282 A | 6/1993 | Wuchinich | |
| 5,312,329 A | 5/1994 | Beaty et al. | |
| 5,465,468 A | 11/1995 | Manna | |
| 5,527,273 A | 6/1996 | Manna et al. | |
| 5,769,211 A | 6/1998 | Manna et al. | |

| | | | |
|---|---|---|---|
| 6,033,375 A | 3/2000 | Brumbach | |
| 6,036,667 A | 3/2000 | Manna et al. | |
| 6,270,471 B1 | 8/2001 | Hechel et al. | |
| 6,375,648 B1 | 4/2002 | Edelman et al. | |
| 6,379,371 B1 | 4/2002 | Novak et al. | |
| 6,443,969 B1 | 9/2002 | Novak et al. | |
| 6,454,730 B1 | 9/2002 | Hechel et al. | |
| 6,461,314 B1 | 10/2002 | Pant et al. | |
| 6,492,762 B1 | 12/2002 | Pant et al. | |
| 6,582,440 B1 | 6/2003 | Brumbach | |
| 6,613,056 B1 | 9/2003 | Brumbach et al. | |
| 6,648,839 B2 | 11/2003 | Manna et al. | |
| 6,736,814 B2 | 5/2004 | Manna et al. | |
| 6,787,974 B2 | 9/2004 | Fjield et al. | |
| 6,799,729 B1 | 10/2004 | Voic | |
| 6,869,439 B2 | 3/2005 | White et al. | |

(Continued)

FOREIGN PATENT DOCUMENTS

| | | |
|---|---|---|
| CA | 186673 S | 3/2021 |
| CN | 102858258 B | 2/2016 |

(Continued)

*Primary Examiner* — Katherine M Shi

(74) *Attorney, Agent, or Firm* — COOLEY LLP

(57) ABSTRACT

In some embodiments, a sheath assembly may include a deformable sheath disposable around an ultrasonic probe including a curved section. The deformable sheath can include a deformable section configured to deform according to the curved section of the ultrasonic probe. The sheath assembly further includes one or more rigid sections coupleable to the deformable sheath, the one or more rigid sections configured to maintain a separation between the ultrasonic probe and the one or more rigid sections to reduce transfer of ultrasonic vibrations generated by the ultrasonic probe through the one or more rigid sections to a user grasping the one or more rigid sections.

27 Claims, 15 Drawing Sheets

(56) References Cited

U.S. PATENT DOCUMENTS

| | | | |
|---|---|---|---|
| 6,902,536 | B2 | 6/2005 | Manna et al. |
| 7,223,267 | B2 | 5/2007 | Isola et al. |
| 7,442,168 | B2 | 10/2008 | Novak et al. |
| 7,717,913 | B2 | 5/2010 | Novak et al. |
| 7,776,027 | B2 | 8/2010 | Manna et al. |
| 7,931,611 | B2 | 4/2011 | Novak et al. |
| 8,025,672 | B2 | 9/2011 | Novak et al. |
| 8,109,925 | B2 | 2/2012 | Voic et al. |
| 8,343,178 | B2 | 1/2013 | Novak et al. |
| 8,353,912 | B2 | 1/2013 | Darian et al. |
| 8,430,897 | B2 | 4/2013 | Novak et al. |
| 8,659,208 | B1 | 2/2014 | Rose et al. |
| 8,690,783 | B2 | 4/2014 | Sinelnikov |
| 8,698,377 | B2 | 4/2014 | Sinelnikov |
| 8,814,870 | B2 | 8/2014 | Paraschiv et al. |
| 8,894,673 | B2 | 11/2014 | Darian |
| 9,070,856 | B1 | 6/2015 | Rose et al. |
| 9,095,367 | B2 | 8/2015 | Olson et al. |
| 9,211,137 | B2 | 12/2015 | Voic |
| 9,320,528 | B2 | 4/2016 | Voic et al. |
| 9,387,005 | B2 | 7/2016 | Voic |
| 9,622,766 | B2 | 4/2017 | Voic |
| 9,636,187 | B2 | 5/2017 | Voic |
| 9,693,792 | B2 | 7/2017 | Novak et al. |
| 9,743,946 | B2 | 8/2017 | Faller et al. |
| 9,872,697 | B2 | 1/2018 | Voic |
| 9,949,751 | B2 | 4/2018 | Voic |
| 10,076,349 | B2 | 9/2018 | Voic |
| 10,092,308 | B2 | 10/2018 | Mikus et al. |
| 10,092,741 | B2 | 10/2018 | Darian |
| 10,117,666 | B2 | 11/2018 | Voic |
| 10,182,837 | B2 | 1/2019 | Isola et al. |
| 10,206,704 | B2 | 2/2019 | Voic et al. |
| 10,299,809 | B2 | 5/2019 | Mikus et al. |
| 10,398,463 | B2 | 9/2019 | Darian et al. |
| 10,398,465 | B2 | 9/2019 | Darian |
| 10,405,875 | B2 | 9/2019 | Voic et al. |
| 10,441,308 | B2 | 10/2019 | Robertson |
| 10,463,381 | B2 | 11/2019 | Voic et al. |
| 10,470,788 | B2 | 11/2019 | Sinelnikov |
| 10,470,789 | B2 | 11/2019 | Mikus et al. |
| 10,471,281 | B2 | 11/2019 | Mikus |
| 10,543,012 | B2 | 1/2020 | Pantano |
| 10,779,848 | B2 | 9/2020 | Houser |
| 10,835,276 | B2 | 11/2020 | Voic et al. |
| 10,842,587 | B2 | 11/2020 | Mikus et al. |
| 11,007,308 | B2 | 5/2021 | Payne et al. |
| 11,173,327 | B2 | 11/2021 | Cotter et al. |
| 11,191,553 | B2 | 12/2021 | Ketelhohn et al. |
| 11,284,915 | B2 | 3/2022 | Cotter et al. |
| 11,298,434 | B2 | 4/2022 | Isola et al. |
| 11,317,936 | B2 | 5/2022 | James et al. |
| 11,324,531 | B2 | 5/2022 | Voic et al. |
| 11,672,558 | B2 | 6/2023 | Voic |
| 11,674,831 | B2 | 6/2023 | DeKalb |
| 11,690,641 | B2 | 7/2023 | Stulen et al. |
| 11,737,775 | B2 | 8/2023 | Voic et al. |
| 11,738,215 | B2 | 8/2023 | Cotter et al. |
| 11,950,790 | B2 | 4/2024 | Voic |
| 12,011,190 | B2 | 6/2024 | Theodore et al. |
| 12,138,489 | B2 | 11/2024 | Cotter et al. |
| 12,279,787 | B2 | 4/2025 | Ellegala |
| 12,402,905 | B2 | 9/2025 | Levy et al. |
| 2006/0052774 | A1 | 3/2006 | Garrison et al. |
| 2007/0173871 | A1* | 7/2007 | Houser .......... A61B 17/320092 |
| | | | 606/169 |
| 2013/0226042 | A1 | 8/2013 | Novak et al. |
| 2013/0231528 | A1 | 9/2013 | Voic |
| 2014/0180002 | A1 | 6/2014 | Voic |
| 2014/0277034 | A1 | 9/2014 | Darian |
| 2015/0088137 | A1 | 3/2015 | Manna |
| 2015/0094723 | A1 | 4/2015 | Darian |
| 2015/0320437 | A1* | 11/2015 | Worrell .......... A61B 17/320068 |
| | | | 606/169 |
| 2017/0354429 | A1 | 12/2017 | Ketelhohn et al. |
| 2021/0267622 | A1 | 9/2021 | Ellegala |
| 2023/0048993 | A1 | 2/2023 | Levy et al. |
| 2023/0210549 | A1 | 7/2023 | Voic et al. |

FOREIGN PATENT DOCUMENTS

| | | |
|---|---|---|
| CN | 107205763 B | 11/2020 |
| CN | 113543733 A | 10/2021 |
| CN | 221786351 U | 10/2024 |
| EP | 4262572 A1 | 10/2023 |
| ES | 2390565 T3 | 11/2012 |
| WO | WO-2015129943 A1 | 9/2015 |
| WO | WO-2015129945 A1 | 9/2015 |
| WO | WO-2016075745 A1 | 5/2016 |
| WO | WO-2017187345 A1 | 11/2017 |
| WO | WO-2020157682 A1 | 8/2020 |

* cited by examiner

UN-ASSEMBLED

ASSEMBLED

SECTION A-A
SCALE 1:1

SECTION A-A
SCALE 1:1

SHEATHS FOR ULTRASONIC SURGICAL DEVICES, AND SYSTEMS, COMPONENTS, AND METHODS THEREOF

TECHNICAL FIELD

This disclosure describes systems, devices, and methods for covering ultrasonic surgical instruments. More specifically, the disclosure herein relates to a sheath assembly for an ultrasonic surgical probe.

BACKGROUND

Ultrasonic ablation tools are recognized for their accuracy, reliability and ease of use. During surgical procedures, ultrasonic surgical instruments, including the probe at the distal end, vibrate at high frequency and can generate high levels of heat due to prolonged contact between the ultrasonic surgical instrument and external materials (e.g., tissue, protective covers, etc.). The generation of heat can cause pain or injury when the probe has prolonged contact with the patient and/or surgeon. The systems and devices described herein provide protective coverings for ultrasonic surgical probes without hindering the maneuverability, precision, or functionality of the probe.

SUMMARY

In some embodiments, an apparatus comprises a deformable sheath disposable around an ultrasonic probe including a curved section, the deformable sheath including a deformable section configured to deform according to the curved section of the ultrasonic probe; a first rigid section coupleable to the deformable sheath on a first side of the deformable section; and a second rigid section coupleable to the deformable sheath on a second side of the deformable section, the first rigid section and the second rigid section when coupled to the deformable sheath defining a gap therebetween such that the deformable section can deform up to a predetermined angle from a longitudinal axis of a proximal portion of the deformable sheath, the first rigid section and the second rigid section configured to maintain a separation between the ultrasonic probe and an inner surface of the first rigid section and the second rigid section to reduce transfer of ultrasonic vibrations generated by the ultrasonic probe through the first rigid section and the second rigid section to a user grasping the first rigid section or the second rigid section.

In some embodiments, an apparatus comprises a deformable sheath disposable around an ultrasonic probe including a curved section, the deformable sheath including a deformable section configured to deform according to the curved section of the ultrasonic probe; a first rigid section configured to be disposed around the deformable sheath on a first side of the deformable section; and a second rigid section configured to be disposed around the deformable sheath on a second side of the deformable section, the deformable sheath including at least one surface feature on an outer surface thereof, the at least one surface feature configured to engage the first rigid section to align the first rigid section relative to the second rigid section and the deformable section.

In some embodiments, an apparatus, comprises a deformable sheath disposable around an ultrasonic probe including a curved section, the deformable sheath including a deformable section configured to deform according to the curved section of the ultrasonic probe, the deformable sheath configured to define a spacing between an inner surface of the deformable sheath and an outer surface of the ultrasonic probe, the spacing being configured to deliver a fluid to a distal end of the ultrasonic probe; a first rigid section configured to be disposed around a proximal portion of the ultrasonic probe; and a second rigid section configured to be disposed around a distal portion of the deformable sheath, the first rigid section and second rigid sections configured to maintain a separation between the ultrasonic probe and an inner surface of the first rigid section and the second rigid section to reduce transfer of ultrasonic vibrations generated by the ultrasonic probe through the first sections and the second rigid section to a user grasping the first rigid section or the second rigid section.

In some embodiments, an apparatus comprises a deformable sheath disposable around a portion of an ultrasonic probe, the deformable sheath including a deformable section configured to bend omnidirectionally to accommodate a geometry of an ultrasonic probe, a first rigid section coupleable to a first end portion of the deformable sheath; a second rigid section coupleable to a second end portion of the deformable sheath, the second end portion of the deformable sheath, when the first rigid section and second rigid section are coupled thereto, being configured to bend up to a predetermined angle relative to a longitudinal axis of the first end portion of the deformable sheath, the first rigid section and the second rigid section being configured to be spaced no more than a maximum distance from one another to prevent pressure applied by the user to the apparatus from being applied through the deformable sheath to the ultrasonic probe.

BRIEF DESCRIPTION OF THE DRAWINGS

FIGS. 6A-7B show different views of the ultrasonic probe and sheath assembly of FIGS. 4-5.

DETAILED DESCRIPTION

Ultrasonic ablation tools are recognized for their accuracy, reliability and ease of use in cutting through bone and soft tissue. Access to surgical sites is typically gained through a channel or trocar; therefore, surgical probes may be elongated and/or include angled portions to improve visibility of and access to the surgical site. However, elongated probes can make control over fine movements more challenging for the surgeon (i.e., the user or the operator) when the surgeon grips the ultrasonic instrument at the handle. Therefore, it may be advantageous for the ultrasonic surgical instrument to include a sheath or covering along the probe that can be gripped to improve the surgeon's control over a distal tip of the probe. During surgical procedures, ultrasonic surgical instruments, including the probe or end effector at the distal end, vibrate at high frequency and generate high levels of heat when there is prolonged contact between the probe and an external material. The generation of heat can cause pain or injury if the probe and/or sheath comes into prolonged contact with the patient and/or surgeon. The ultrasonic surgical instrument can be configured to deliver fluid through the sheath toward the distal tip of the probe, and a user placing one hand on the sheath distal of the handpiece can experience a burning or stinging sensation in that hand. This sensation can depend on the compressive pressure the surgeon applies to the sheath with the hand. Typical curved surgical instruments are covered solely with flexible, collapsable sheaths which provided limited, end user protection during incidental contact. The embodiments described herein include non-collapsable, flexible sheaths or coverings for ultrasonic instruments that provide the end user with protection against burns when holding the instrument distally at a location where such grasp is not possible when using collapsable sheaths.

Embodiments described herein include a sheath assembly configured to cover the end effector (i.e., the probe) of an ultrasonic surgical instrument to protect the end user. The embodiments described herein provide a sheath for an ultrasonic probe configured to reduce or eliminate discomfort when gripping portions of the probe distal to the handle assembly while accommodating the geometry of the probe. In some embodiments, the sheath assembly may be configured to bend to accommodate an angle of the ultrasonic probe. In some embodiments, the sheath assembly may be configured to maintain a predetermined gap or spacing between the probe and an inner surface of the sheath such that fluid can flow through the sheath without obstruction or blockage. The sheath assembly may include one or more rigid portions configured to enclose at least a portion of the probe and prevent the user from applying pressure (directly or indirectly) to the ultrasonic probe.

Figure 1:
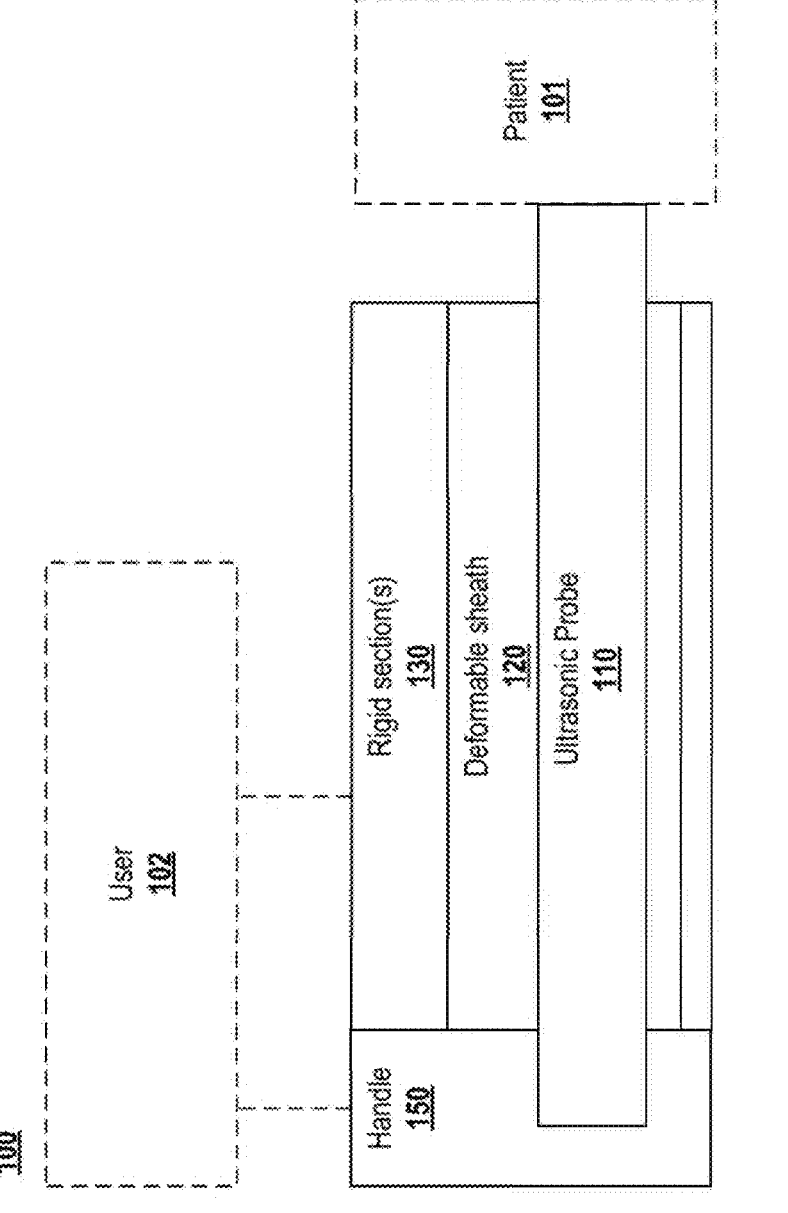
FIG. 1 is a schematic block diagram of a sheath assembly for covering an ultrasonic probe, according to embodiments.

FIG. 1 shows an ultrasonic instrument 100 including a handle 150 and an ultrasonic probe 110 extending from the handle 150. The ultrasonic probe 110 (i.e., "probe") can be configured to cut hard tissue (e.g., bone) or soft tissue at a surgical site within a patient 101. The probe 110 can include a main body and a distal tip configured to interface with tissue within the patient 101. The ultrasonic instrument 100 may include a sheath assembly configured to be disposed around at least a portion of the probe 110. The sheath assembly may be configured to enclose at least a portion of the main body of the ultrasonic probe 110, and the distal tip of the probe 110 may be exposed and configured to contact the patient 101.

In some embodiments, the probe 110 may include a tapered portion and/or may decrease in diameter from a proximal end of the probe 110 to the distal tip. In some embodiments, the probe 110 may be a straight probe. In some embodiments, the probe 110 (e.g., the main body of the probe) may include an angled or curved portion. In some embodiments, the angled or curved portion of the probe 110 may between about 0 degrees (i.e., straight) and about 20 degrees, inclusive of all values and subranges therebetween. In some embodiments, the probe 110 may have a radius of curvature in a range of 3 in to straight (i.e., infinite radius of curvature), inclusive of all values and subranges therebetween.

In some embodiments, the sheath assembly may be configured to accommodate a geometry or shape of the probe 110. In some embodiments, the sheath assembly may include one or more deformable sheath(s) 120 (i.e., deformable portions, sleeves, covers, etc.) configured to be disposed around at least a portion of the probe 110. In some embodiments, the deformable sheath(s) 120 may include a tapered portion corresponding to the shape of the probe 110. In some embodiments, the deformable sheath(s) 120 may include a deformable section (e.g., a joint, hinge, etc.) configured to deform according to the curved or angled section of the probe 110. In some embodiments, the deformable section may have a predetermined length. In some embodiments, the bellowed section may have a length between about 4 mm and about 10 mm, inclusive of all values and subranges therebetween. In some embodiments, the deformable section of the deformable sheath(s) 120 may include a bellowed section (i.e., a ribbed, corrugated, or accordion-like section). In some embodiments, the bellowed section may be capable of omnidirectional bending. The bellowed section can be configured to bend according to a curvature of the curved section of the probe 110 when the deformable sheath 120 is disposed around the probe 110. In some embodiments, the bellowed section may have a predetermined number of ridges or corrugations in a range between about 1 ridge to about 10 ridges, inclusive of all values and subranges therebetween. In some embodiments, the deformable section can be configured to deform or bend relative to a longitudinal axis of the handle 150 and/or relative to a proximal portion of the deformable sheath 120. In some embodiments, the deformable section can bend to an angle relative to the longitudinal axis of up to about 5 degrees, about 10 degrees, about 15 degrees, about 20 degrees, about 25 degrees, about 30 degrees, inclusive of all values and ranges therebetween. In other words, the deformable section can bend such that the distal portion of the deformable sheath 120 and the proximal section of the deformable sheath form the predetermined angle therebetween. In some embodiments, the predetermined angle may be about 11 degrees.

In some embodiments, the sheath assembly may include one or more rigid sections 130 (i.e., rigid sheath(s), sleeves, covers, shells, etc.) configured to be coupled to at least a portion of the deformable sheath(s) 120, the probe 110, and/or the handle 150. In some embodiments, the sheath assembly may include one deformable sheath 120 configured to be disposed around the probe 110 and including an angled or curved section corresponding to the shape of the probe 110. The sheath assembly may further include one rigid sheath 130 configured to be disposed around the deformable sheath 120. The rigid sheath 130 may include an angled or curved section corresponding to the shape of the probe 110 and the deformable sheath 120.

In some embodiments, the sheath assembly may include a plurality of rigid sections 130 coupleable to the deformable sheath 120, the probe 110 and/or the handle 150. In some embodiments, the sheath assembly may include a first rigid section coupleable to a first portion (e.g., a proximal portion) of the deformable sheath 120 and a second rigid section coupleable to a second portion (e.g., a distal portion) of the deformable sheath 120. In some embodiments, the first rigid section may be configured to be disposed around the deformable sheath 120 on a first side of the deformable section. In some embodiments, the second rigid section may be configured to be disposed around the deformable sheath 120 on a second side of the deformable section. Therefore, the deformable sheath 120 and the rigid section(s) 130 may collectively enclose a length of the probe 110. In some embodiments, an inner diameter of the rigid sheath(s) may be configured to fit around an outer diameter of the deformable sheath 120 such that an inner surface of the rigid sheath(s) 130 contact an outer surface of the deformable sheath(s) 120 along at least a portion of a length of the sheath assembly.

In some embodiments, a distal end of the first rigid section may be configured to be disposed within a proximal end of the deformable sheath 120 to couple the second rigid section to the deformable sheath 120 (see, for example, FIGS. 11A-11D). Therefore, the rigid section 130 may enclose a first portion of the probe 110 and the deformable sheath 120 may enclose a second portion of the probe 110. In some embodiments, the proximal end of the deformable sheath 120 may be configured to fit over a distal portion of the first rigid section to secure the first rigid section to the deformable sheath 120. In some embodiments, the distal end portion of the first rigid sheath 130 may include a form-locking feature configured to prevent accidental decoupling of the first rigid sheath 130 and the deformable sheath. For example, the form-locking feature may prevent the deformable sheath 120 and the rigid sheath 130 from slipping relative to one another.

The rigid section(s) 130 may be configured to maintain a separation between the probe 110 and an inner surface of the rigid section(s) 130 to reduce (or prevent) transfer of ultrasonic vibrations generated by the probe through 110 through the rigid section(s) 130 to a user or operator 102 grasping the rigid section(s) 130. Deformable sheaths 120 may be deformed when held by the user 102, which can cause the deformable sheath 120 to press against the probe 110 and transfer the ultrasonic vibrations through the deformable sheath 120 and to the hand of the user 102. However, the rigid section(s) 130 may include a rigid material (e.g., non-deformable) such that the user cannot press the deformable sheath against the probe 110 and/or apply pressure (directly or indirectly) to the probe 110 when gripping the rigid section(s) 130.

In some embodiments, the sheath assembly may be configured to form a joint (e.g., deformable section, hinge, junction, etc.) configured to bend according to the curved or angled section of the probe 110. For example, the rigid section(s) 130, when coupled to the deformable section, may be aligned relative to one another and relative to the deformable section such that the deformable section can deform or bend according to the curved portion of the probe 110. For example, the first rigid section and the second rigid section when coupled to the deformable sheath can define a gap therebetween such that the deformable section can deform up to a predetermined angle from the longitudinal axis of the proximal portion of the deformable sheath 120 (e.g., the distal end of the deformable sheath 120 can bend up to the predetermined angle relative to the proximal portion of the deformable sheath 120).

In some embodiments, the first rigid section and the second rigid section may be substantially straight or linear. Therefore, the first rigid section and the second rigid section, when coupled to the deformable section 120, may be configured to define a gap therebetween configured to align with the deformable section of the deformable sheath 120 and the curved section of the probe 110. In some embodiments, a diameter (e.g., inner diameter and/or outer diameter) of one of the rigid sections may be enlarged near the joint (e.g., the curved section of the probe 110) such that the rigid sections 130 can move relative to one another around a pivot point of the sheath assembly without colliding. For example, the enlarged section may provide space for movement of the rigid section 130 around the pivot point before the rigid surface contacts the probe 110 and/or the other rigid section 130.

In some embodiments, the deformable sheath 120 may include one or more surface features (e.g., ridges, ledges, steps, indentations, protrusions, etc.), and the rigid section(s) 130 may be disposable on the deformable sheath 120 in engagement with the one or more surface features. In some embodiments, the one or more surface features may be configured to align the rigid section(s) 130 relative to each other and relative to the deformable section. In some embodiments, the one or more surface features may align the first rigid section and the second rigid section such that they define a gap around at least a portion of the deformable section. For example, the one or more surface features may be disposed on either side of the deformable section of the deformable sheath 120 to hold the rigid sheath(s) in place relative to the deformable section (and the curved section of the probe 110). The surface feature(s) may be configured to prevent the rigid sheath(s) from covering the deformable section and preventing the deformable section from bending. In some embodiments, the surface feature(s) may include a ridge of bellowed section of the deformable section of the deformable sheath 120. In some embodiments, the surface feature(s) may include ledges disposed adjacent to the deformable section (e.g., ledges on either side of the deformable section). In some embodiments, a first surface feature may include a ledge configured to engage the first rigid section to align or space the first rigid section relative to the second rigid section. In some embodiments, a second surface feature may be a ledge configured to engage the second rigid section to align or space the first rigid section relative to the first rigid section.

In some embodiments, the deformable sheath 120 may include a pair of surface features (e.g., ledges) configured to hold the second rigid section therebetween around a distal portion of the deformable sheath 120 (e.g., to prevent the rigid sheath from sliding over the deformable section and/or over the distal tip of the probe 110). The pair of surface features may include a first surface feature near the deformable section and a second surface feature near a distal end of the probe 110. In some embodiments, the first rigid sheath may be configured to fit between a first pair of surface features on a proximal side of the deformable section of the deformable sheath 120 and/or the second rigid sheath may be configured to fit between a second pair of surface features on a distal side of the deformable section of the deformable sheath 120. In some embodiments, an outer surface of the rigid sheath(s) 130 may form a seamless surface with neighboring sections of the deformable sheath(s) 120 such that the user can move their hand along the sheath assembly without hitting edges readjusting grip. In some embodiments, the deformable sheath 120 may define a first indentation having a length corresponding to a length of the rigid section and a height equivalent to a thickness of the rigid section such that the rigid section sits flush with an outer surface of the deformable sheath 120 and forms a seamless surface. The deformable sheath 120 may define a second indentation having a length corresponding to a length of the second rigid section and a height equivalent to a thickness of the second rigid section such that the second rigid section sits flush with an outer surface of the deformable sheath 120 and forms a seamless surface. In some embodiments, the deformable sheath 120 may include one or more surface features configured to provide haptic feedback indicative of a location of the deformable section.

In some embodiments, the first rigid section and the second rigid section may be coupled to the deformable sheath 120 such that the first rigid section and the second rigid section define a distance (e.g., gap, space, etc.) therebetween such that the deformable sheath can deform. However, the gap may be sufficiently small to prevent a user from pressing the deformable sheath against the ultrasonic probe. For example, the first rigid section and the second rigid section may define a gap through which a finger of the user 102 cannot fit such that the user 102 cannot contact (or firmly press) the deformable sheath 120, thereby preventing the user 102 from being exposed to the ultrasonic vibrations of the probe 110. In some embodiments, the first rigid section and the second rigid section may be configured to be spaced no more than a maximum distance from one another to prevent pressure applied by the user to the apparatus from being applied through the deformable sheath to the ultrasonic probe. In some embodiments, the gap between the first rigid section and the second rigid section may have a maximum horizontal distance in range between about 1 mm and about 12 mm, inclusive of all values and subranges therebetween. In some embodiments, the gap between the first rigid section and the second rigid section may have a maximum horizontal distance in range between about 2 mm and about 8 mm, inclusive of all values and subranges therebetween.

In some embodiments, the rigid section(s) 130 may have a portion configured to extend over the deformable section of the deformable sheath 120 to decrease an amount of the deformable sheath 120 that is exposed. In some embodiments, at least one of the first rigid section or the second rigid section may include the enlarged section. The enlarged section can be configured to be disposed around the deformable section of the deformable sheath 120. The enlarged section may provide space to accommodate a curvature of the probe and deformable section while covering the deformable sheath 120. The enlarged section may have increase in an diameter and/or outer diameter to provide space for the deformable sheath and probe to curve while providing protection around the deformable sheath 120 and probe 110. In some embodiments, the first rigid section may include an enlarged distal portion configured to be disposed around the deformable section of the deformable sheath and the angled portion of the probe. In some embodiments, the second rigid section may include an enlarged proximal portion configured to be disposed around the deformable section of the deformable sheath and the angled portion of the probe.

The sheath assembly can be coupleable to the handle 150 to secure the sheath assembly relative to the probe 110. In some embodiments, the deformable sheath 120 may be configured to be coupled to or engage with the handle 150. In some embodiments, the deformable sheath 120 may be coupleable to a connector that connects the deformable sheath to the handle 150. In some embodiments, the deformable sheath 120 can include a lip, ridge, or projection at a proximal end thereof configured to indicate a proper orientation of the deformable sheath 120 relative to the handle 150 such that the deformable sheath 120 can couple to the handle 150. In some embodiments, one of the rigid section(s) 130 may be configured to be coupled to or engage with the handle 150 or a connector that connects the rigid sheath 130 to the handle 150. In some embodiments, the connector or handle may include a locking feature configured to prevent axial motion of the deformable sheath relative to the connector or handle. In some embodiments, the locking feature may include a protrusion (e.g., raised portion, bump, protrusion, ledge, projection, etc.) configured to fit into a divot or cavity defined in an inner surface of the deformable sheath, as shown. In some embodiments, the protrusion may extend around a circumference of the connector or handle and fit into a divot that extends circumferentially around an inner surface of the deformable sheath. In some embodiments, the deformable sheath may be configured to form a slip fit with the connector or handle to allow for omnidirectional orientation (e.g., such that the deformable sheath can be coupled to the connector or handle at any orientation).

The sheath assembly may form a channel around the probe 110 configured to convey fluid from a fluid supply to the distal tip of the probe 110 and/or the surgical site near the distal tip of the probe 110. In some embodiments, the handle 150 can include a port configured to couple to a fluid supply to convey fluid from the handle 150, through the channel, and to the distal tip of the probe 110. In some embodiments, the one or more rigid sections 130 may define a port or channel coupleable to the fluid supply to convey fluid to distal tip of the probe. In some embodiments, a proximal end of the first rigid sheath (e.g., the proximal sheath) may be configured to engage the handle 150 and a distal end of the first rigid sheath may be configured to be coupled to the deformable sheath 120. In some embodiments, the deformable sheath 120 (e.g., a proximal end of the deformable sheath 120) may define a port or a first channel configured to be coupled to a fluid supply and convey fluid to a second channel defined around the probe 110.

In some embodiments, the sheath assembly (the deformable sheath 120 and/or the rigid sheath(s) 130) may maintain a spacing between an outer surface of the probe and an inner surface of the sheath assembly along at least a portion of the probe 110 that is above predetermined threshold distance to allow fluid to flow without blockage or pressure build up. In some embodiments, the deformable sheath 120 may include one or more protrusions configured to maintain the spacing (e.g., the predetermined spacing) between an inner surface of the deformable sheath and an outer surface of the ultrasonic probe 110, the spacing being configured to deliver a fluid to a distal end of the probe 110. In some embodiments, the deformable sheath 120 and the one or more rigid section(s) 130 may collectively define the channel around the probe. For example, the deformable sheath 120 may define a first portion of the channel and the rigid section(s) 130 (e.g., a proximal rigid section) may define a second portion of the channel. In some embodiments, the distance between the probe 110 and the sheath assembly may be smaller at the distal end of the probe 110 than the distance between the probe 110 and the sheath assembly along the main body of the probe 110. In some embodiments, the distance between the probe and the sheath assembly may vary across the length of the probe 110.

Figure 2:
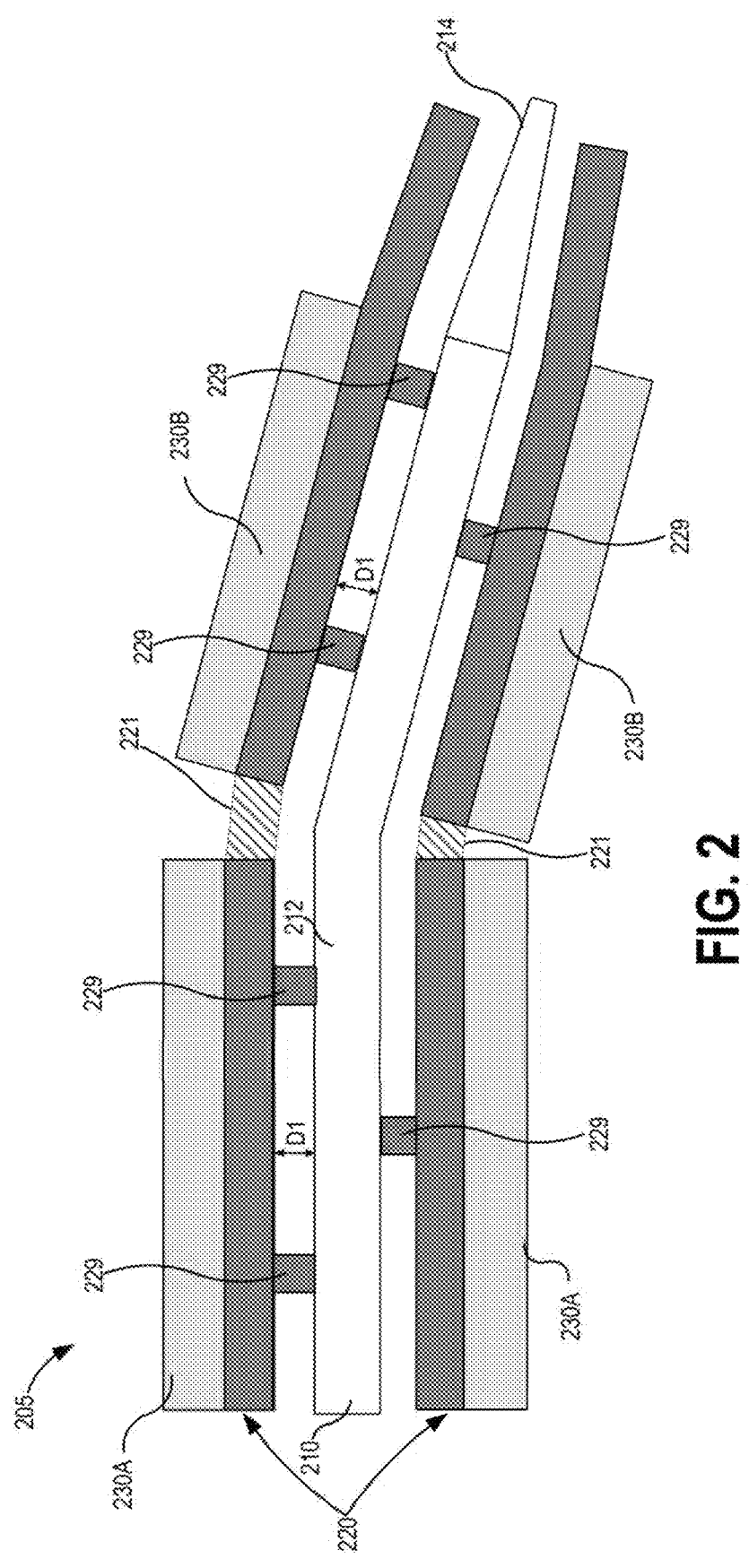
FIG. 2 is a schematic block diagram of a sheath assembly for covering an ultrasonic probe, according to embodiments.

FIG. 2 is a schematic block diagram of a sheath assembly 205 for an ultrasonic probe ("probe") 210, according to embodiments. In some embodiments, the probe 210 includes a probe main body 212 and a distal end 214. In some embodiments, the sheath assembly 205 can include a deformable sheath 220 including a deformable section 221 configured to be disposed around the probe 210. The deformable section 221 of the deformable sheath 220 may be configured to align with and bend along a curve of the probe 210. In some embodiments, a distal end of the deformable sheath 220 may have a geometry (e.g., a taper, radius, or length) according to a geometry of the distal end 214 of the probe 210. The sheath assembly 205 may include a first rigid section 230A configured to be disposed on a proximal side of the deformable section 221 and a second rigid section 230B configured to be disposed on a distal side of the deformable section 221. In some embodiments, the deformable sheath 220 may include one or more protrusions 229 configured to maintain at least a distance of D1 between an outer surface of the main body 212 of the probe 210 and an inner surface of the deformable sheath 220. Therefore, the deformable sheath 220 may define a channel around the probe 210, the channel being configured to convey fluid from a proximal end of the probe to the distal end 214. The distance D1 may correspond to one or more fluid flow parameters desired for the ultrasonic procedure. In some embodiments, the distance D1 between the inner surface of the sheath assembly and the outer surface of the probe 110 may be between about 0.5 mm and about 2 mm, inclusive of all values and subranges therebetween. In some embodiments, the distance D1 between the inner surface of the sheath assembly and an outer surface of the probe 110 may be at least about 0.2 mm. In some embodiments, the distance D1 between the inner surface of the sheath assembly and an outer surface of the probe 110 may no more than about 2 mm. In some embodiments, the one or more protrusions 229 may be spaced or dispersed across the inner surface of the deformable sheath 220 (e.g., along a length and/or radially) such that fluid can flow past the one or more protrusions 229.

In some embodiments, the first rigid section 230A and the second rigid section 230B may be coupled to the deformable sheath 220 such that the first rigid section 230A and the second rigid section 230B define a gap therebetween around the deformable section 221 such that the deformable sheath 220 can form an angle corresponding to an angle of the probe 210. In some embodiments, the gap can be sufficiently small such that the user cannot press down on the deformable section 221 and/or apply pressure to the probe 210. In some embodiments, the rigid sections 230A, 230B may be configured to be spaced from the ultrasonic probe to reduce transfer of vibrations from the probe 210 to the rigid sections 230A, 230B and to a user gripping the rigid sections 230A, 230B. The sheath assembly 205 is structurally and/or functionally similar to the other sheath assemblies described herein, and therefore, certain details of the sheath assembly are not described with respect to FIG. 2.

Figures 3A, 3B, 3C:
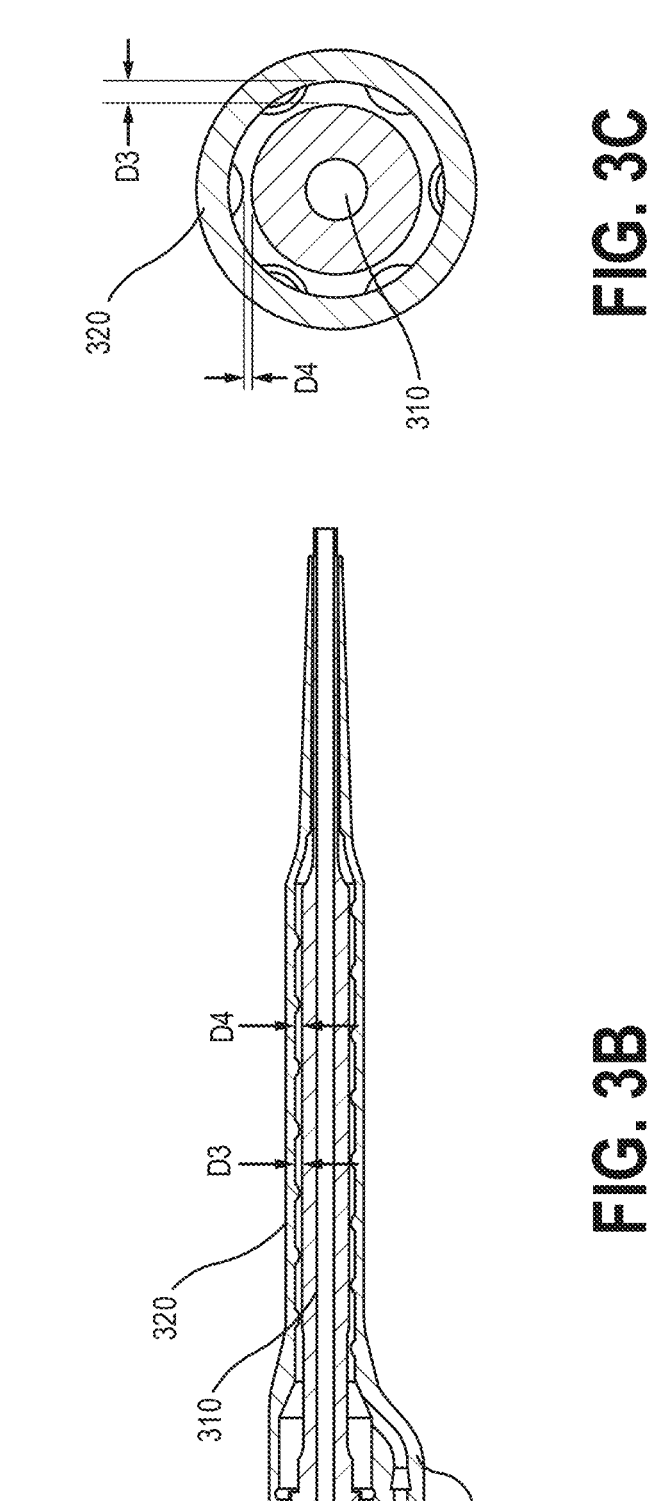
FIG. 3A is a side view of a deformable sheath disposed around a straight ultrasonic probe, according to embodiments.
FIG. 3B is a cross-section along the line D-D of the deformable sheath and ultrasonic probe, according to embodiments.
FIG. 3C is a cross-sectional along E-E of the deformable sheath and ultrasonic probe, according to embodiments.

FIG. 3A is a side view of a deformable sheath 320 disposed around a straight ultrasonic probe 310 ("probe") such that the distal tip of probe extends from a distal end of the deformable sheath 320. FIG. 3B is a cross-section along the line D-D of the deformable sheath 320 disposed around the probe 310. As shown, a proximal portion of the deformable sheath 320 may include a lip, ridge, or projection 322. The lip 322 may define a channel configured to couple to a fluid supply and/or a fluid channel of the handle (not shown).

In some embodiments, the lip 322 may provide visual feedback to inform the user an orientation with which the deformable sheath 320 couples to the handle such that a curved portion of the deformable sheath 320 aligns with a curved portion of the probe 310. In some embodiments, the lip 322 may provide haptic feedback to the user that the user is beginning to grip the sheath assembly 305, and therefore the probe 310. The deformable sheath 320 may define a channel around the probe 310 configured to convey fluid to a distal tip of the probe 310. In some embodiments, the deformable sheath 320 may have a first diameter along a proximal portion and may taper to a second diameter (not shown) smaller than the first diameter along a distal portion of the deformable sheath. In some embodiments, the deformable sheath 320 may be separated from the probe 310 by a distance D3 along the proximal portion of the probe 310. In some embodiments, the distance D3 may be in a range between about 0.2 mm to about 2 mm, inclusive of all values and subranges therebetween. In some embodiments, the deformable sheath 320 may include protrusions that extend from an inner surface of the deformable sheath 320. In some embodiments, the protrusions may be configured to be spaced from the probe at a distance D4. The distance D4 may be in a range between about 0.1 mm to about 0.4 mm, inclusive of all values and subranges therebetween. In some embodiments, the protrusions may be configured to contact the probe to maintain at least the distance D4 between the probe and an inner surface of the deformable sheath 320. FIG. 3C is a cross-sectional along E-E of the deformable sheath 320. The deformable sheath includes one or more protrusions configured to maintain a space between an inner surface of the deformable sheath 320 and an outer surface of the probe. In some embodiments, the one or more protrusions may be spaced from the outer surface of the probe a distance D4 when no compressive pressure is applied to the deformable sheath 320. The one or more protrusions may be distributed along the inner surface of the sheath 320 such that fluid can flow between the one or more protrusions.

Figure 4:
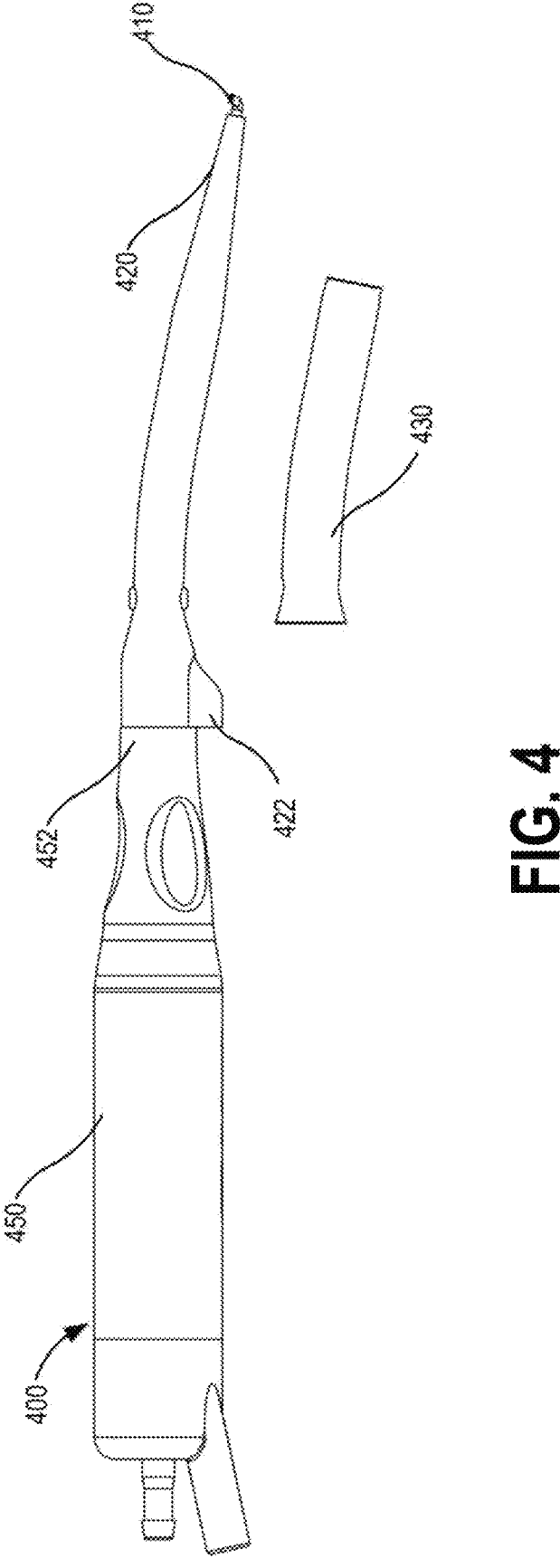
FIG. 4 is a side view of an ultrasonic probe including a deformable sheath disposed around a curved ultrasonic probe, and a rigid sheath separated from the deformable sheath, according to embodiments.
Figure 5:
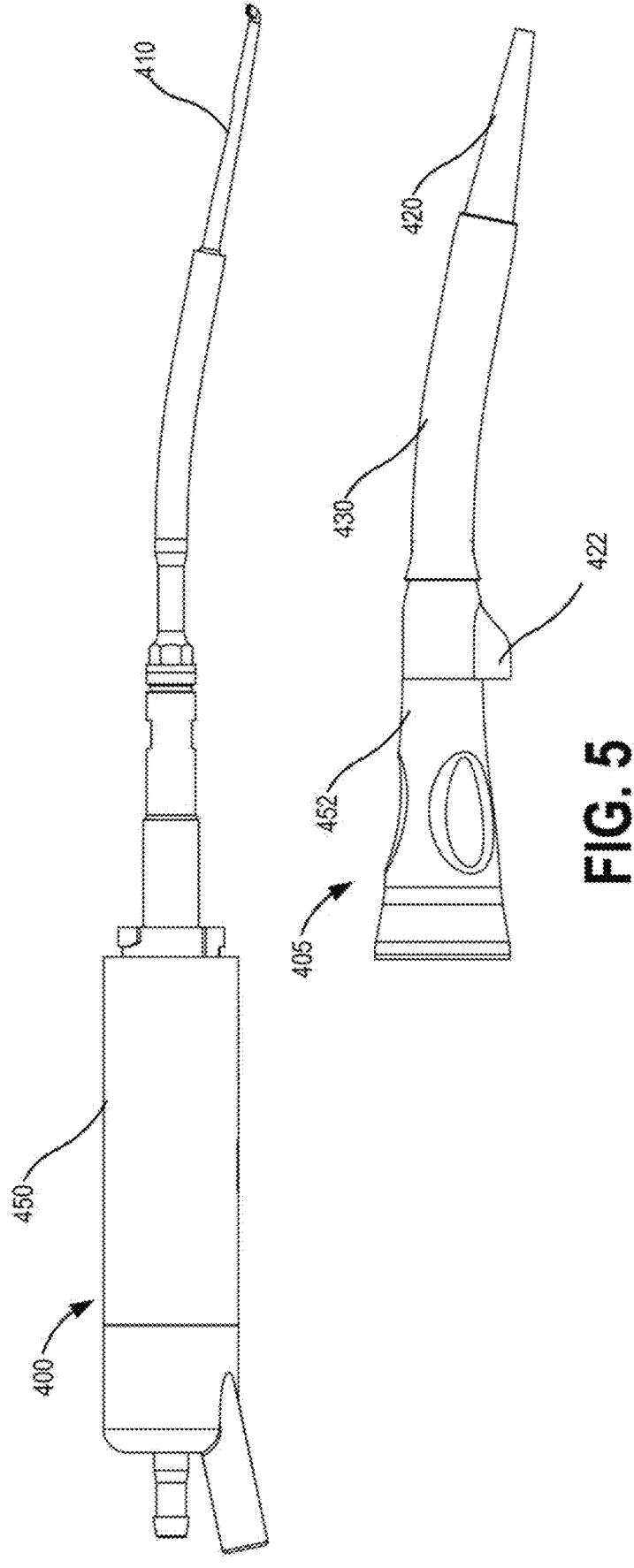
FIG. 5 shows the ultrasonic probe of FIG. 4 with the assembled sheath assembly separated from the ultrasonic probe, according to embodiments.
Figures 6A, 6B, 7A, 7B:
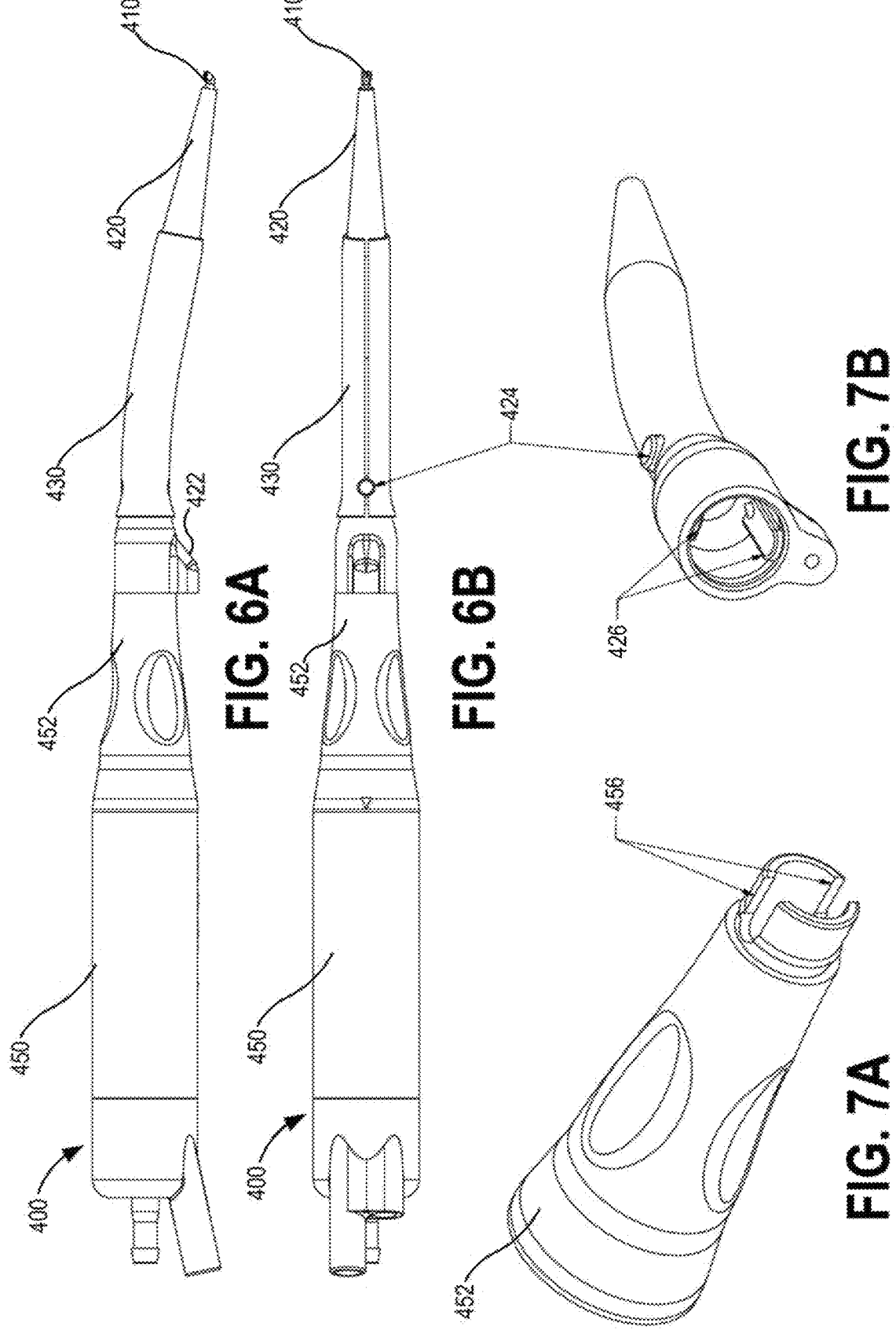

FIG. 4 is a side view of an ultrasonic instrument 400 including the deformable sheath 420 disposed around the probe 410 and a rigid sheath 430 separated from the deformable sheath 420, according to embodiments. A distal tip of the probe 410 extends distal to a distal end of the deformable sheath 420 such that the distal tip of the probe 410 can contact a patient. The deformable sheath 420 can be coupleable to a connector 452 configured to couple the deformable sheath 420 to the handle 450. In some embodiments, the deformable sheath 420 can couple directly to the handle 450. In some embodiments, the connector 452 can include one or more gripping portions or indentations to improve grip of the probe 410 by the user. In some embodiments, the deformable sheath 420 may include a proximal portion having a lip or ridge 422 similar to the lip or ridge 322. The lip or ridge 422 may provide haptic feedback to the user that the user is beginning to grip the sheath assembly 405, and therefore the probe 410. The lips or ridge 422 may define visual feedback to the user and/or may define a channel configured to convey fluid to the probe 410. The deformable sheath 420, when coupled to the connector 452, is configured to curve to a curvature of the probe 410. FIG. 5 shows the ultrasonic instrument 400 of FIG. 4 with the assembled sheath assembly 405 separated from the ultrasonic instrument 400. The rigid sheath 430 may be configured to be disposed over a portion of the deformable sheath 420. In some embodiments, the rigid sheath 430 may have a curvature corresponding to the curvature of the deformable sheath 420 and/or the probe 410 such that an inner surface of the rigid sheath 430 is spaced from the ultrasonic probe along a length of the probe 410. FIGS. 6A-6D show different views of the ultrasonic probe and sheath assembly of FIGS. 4-5. As shown in FIG. 6B and FIG. 7B, the deformable sheath 420 may include a surface feature (e.g., a notch) 424 extending from a surface (e.g., a top side) thereof. The rigid sheath 430 may define an opening configured to receive the notch 424 to lock a position of the rigid sheath 430 relative to the deformable sheath 420. The notch 424 may be configured to align the rigid sheath 430 relative to the probe 410 such that the rigid sheath 430 follows a curvature of the probe 410. FIGS. 7A-7B show one or more engagement features 456 of the connector 452 configured to engage with one or more engagement features 426 of the deformable sheath 420. In some embodiments, the engagement features 456 of the connector 452 may be configured to receive the engagement features 426 of the deformable sheath 420 in a particular orientation such that the geometry of the sheath assembly 405 matches a geometry of the probe 410. The sheath assembly 405 may be structurally and/or functionally similar to the sheath assembly 105, and therefore, certain details of the sheath assembly 405 are not described herein with respect to FIGS. 3A-7B.

Figures 8A, 8B:
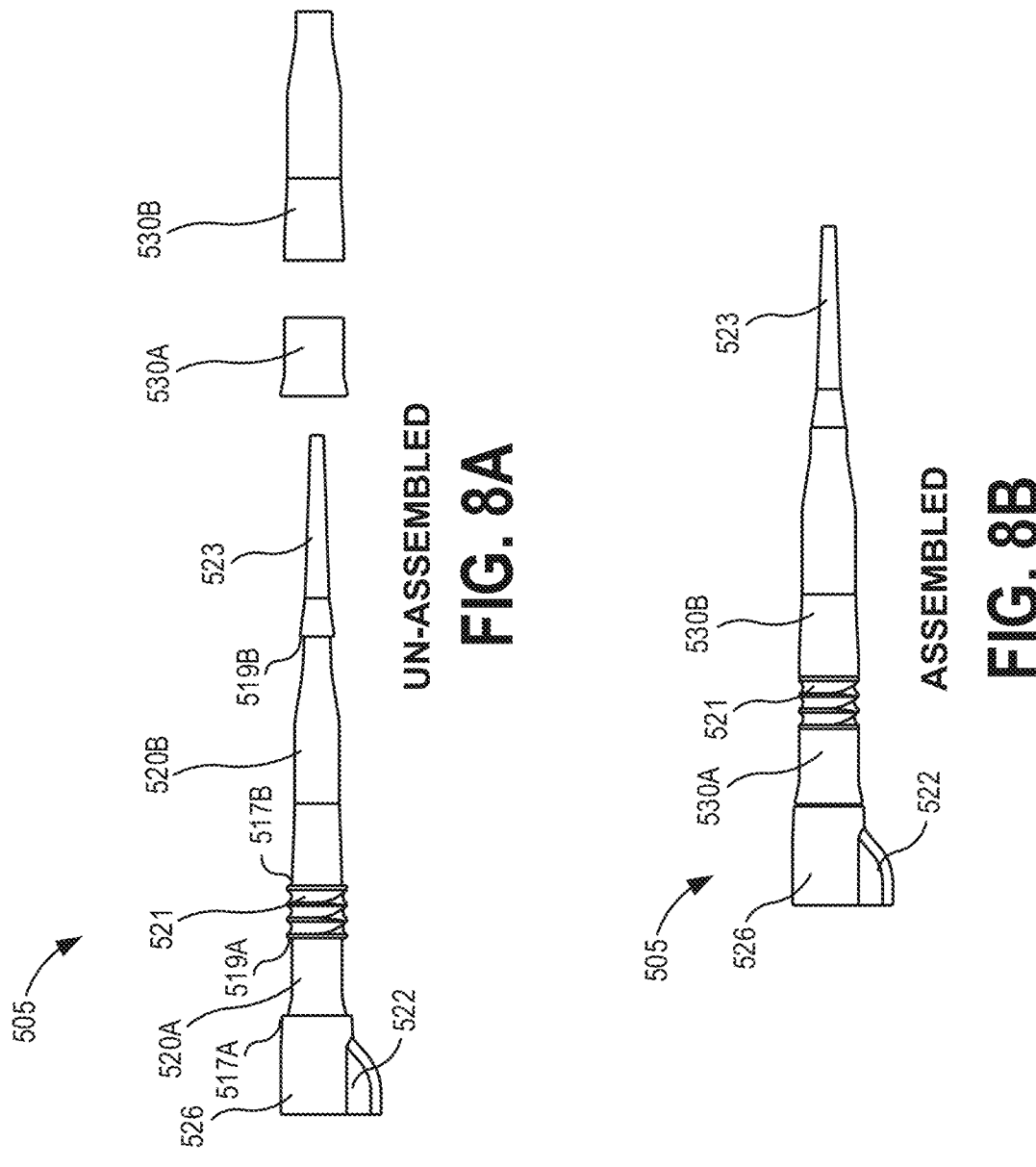
FIGS. 8A-8B show a sheath assembly for an ultrasonic probe in an unassembled and assembled configuration, respectively, according to embodiments.

FIGS. 8A-8B show a sheath assembly 505 for an ultrasonic probe in an unassembled and assembled configuration, respectively. In some embodiments, sheath assembly 505 includes a deformable sheath including a deformable section 521 configured to deform to a curvature of a probe (not shown). The deformable section 521 may be a bellowed section (e.g., accordion-like, corrugated, etc.) configured to bend up to a predetermined angle relative to the longitudinal axis of the handle and/or a proximal end of the deformable sheath. In some embodiments, the deformable section 521 is configured to bend omnidirectionally. In some embodiments, a location of the deformable section 521 along a length of the deformable sheath may correspond to a curved portion of the probe. The deformable sheath includes a proximal portion 520A on a first side of the deformable section 521 and a distal portion 520B on a second side of the deformable section 521. The deformable sheath further includes a distal tip 523 configured to align with a distal end of the probe. Therefore, the distal tip 523 of the deformable sheath may have a geometry (e.g., a taper) corresponding to the taper of the distal end of the probe. A proximal end 526 of the deformable sheath may be configured to couple to a connector or handle. The proximal end 526 may have a lip or ridge 522. The lip or ridge 522 may be similar structurally and/or functionally to the lip or ridge 322 or 422. In some embodiments, the connector or handle may include a locking feature 554 configured to prevent axial motion of the deformable sheath relative to the connector or handle. In some embodiments, the locking feature 554 may include a protrusion (e.g., raised portion, bump, protrusion, ledge, projection, etc.) configured to fit into a divot or cavity defined in an inner surface of the deformable sheath, as shown. In some embodiments, the protrusion may extend around a circumference of the connector or handle and fit into a divot that extends circumferentially around an inner surface of the deformable sheath. In some embodiments, the deformable sheath may be configured to form a slip fit with the connector or handle to allow for omnidirectional orientation (e.g., such that the deformable sheath can be coupled to the connector or handle at any orientation).

Figures 9A, 9B:
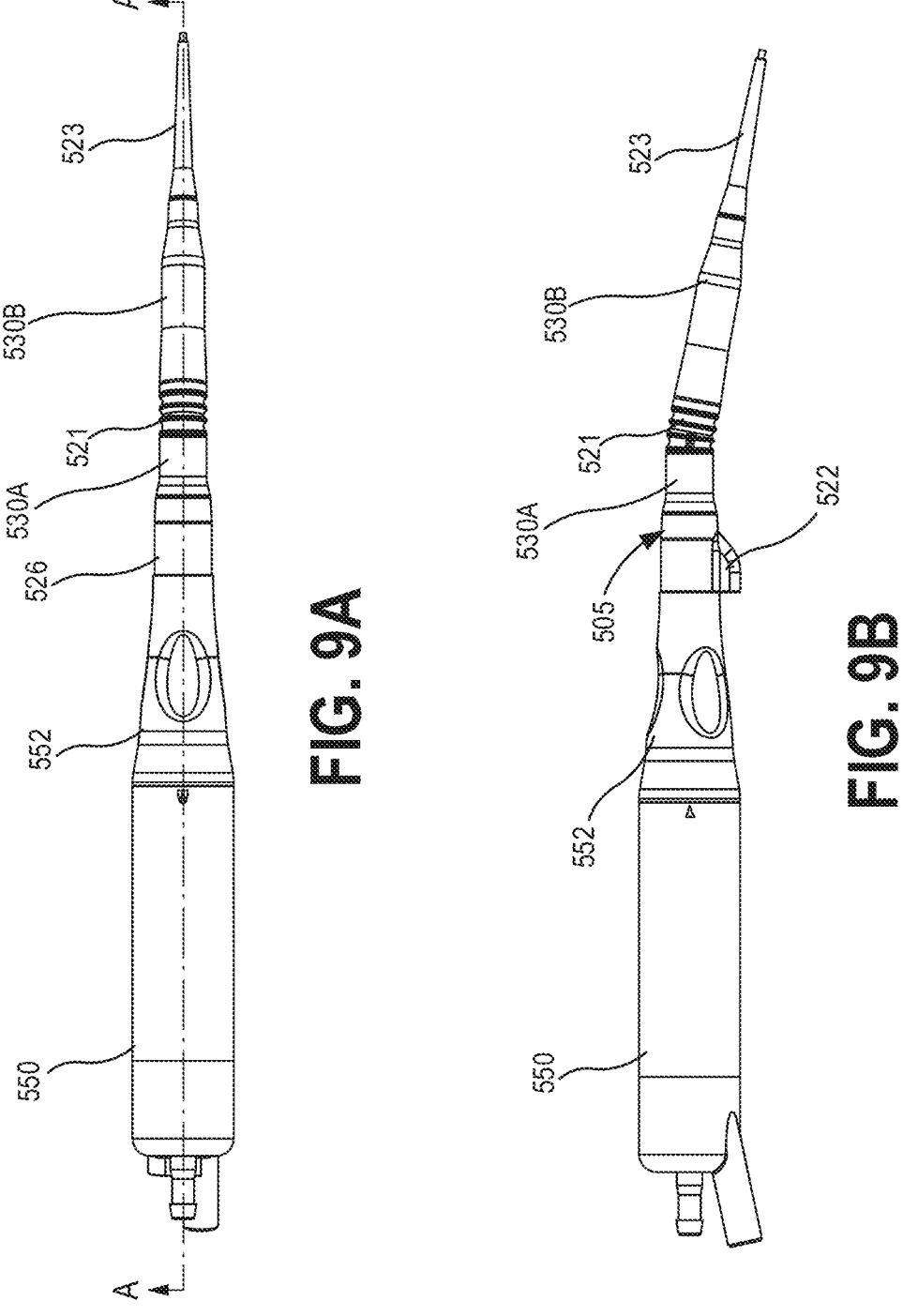
FIGS. 9A-9D show different views of the ultrasonic probe and sheath assembly of FIGS. 8A-8B.

The sheath assembly 505 may further include a first rigid sheath 530A configured to be disposed around a proximal portion 520A of the deformable sheath. The sheath assembly 505 may include a second rigid sheath 530B configured to be disposed around a distal portion 520B of the deformable sheath. The proximal portion 520A of the deformable sheath may include one or more surface features on an outer surface thereof. The rigid sheaths 530A, 530B may be configured to engage with the one or more surface features or ledges 517A, 517B, 519A, 519B when the rigid sheaths 530A, 530B are disposed around the deformable sheath. In some embodiments, the one or more surface features may hold in place or align the rigid sheaths 530A, 530B relative to the deformable sheath. In some embodiments, the first rigid sheath 530A may be disposed between a first pair of surface features 517A, 519A, and the second rigid sheath 530B may be disposed between a second pair of surface features 517B, 519B such that an outer surface of the rigid sheath(s) 530A, 530B form a seamless surface with neighboring sections of the deformable sheath, as shown in FIG. 8B. In other words, the deformable sheath may define a first indentation on a first side of the deformable section 521 between the surface features 517A, 519A and configured to receive the rigid sheath 530A. The deformable sheath may define a second indentation on a second side of the deformable section 521 between the surface features 517B, 519B and configured to receive the second rigid sheath 530B. The first indentation and the second indentation may have a length and height corresponding to a length and thickness of the rigid sheath 530A and second rigid sheath 530B, respectively. The surface features 517A, 517B, 519A, 519B may space the rigid sheath(s) 530A, 530B from the deformable section 521 such that the deformable section 521 can bend, as shown in FIG. 9B. For example, the rigid sheath(s) 530A, 530B may fit on the deformable sheath such that the rigid sheath(s) 530A, 530B define a gap therebetween corresponding to the deformable section 521. The gap may have a length such that the deformable section 521 can bend up to an angle of the probe. As shown in FIGS. 9A-9D, the proximal end of the deformable sheath is configured to be coupled to a connector 552. The connector 552 is configured to couple the sheath assembly to the handle 550.

Figures 9C, 9D:
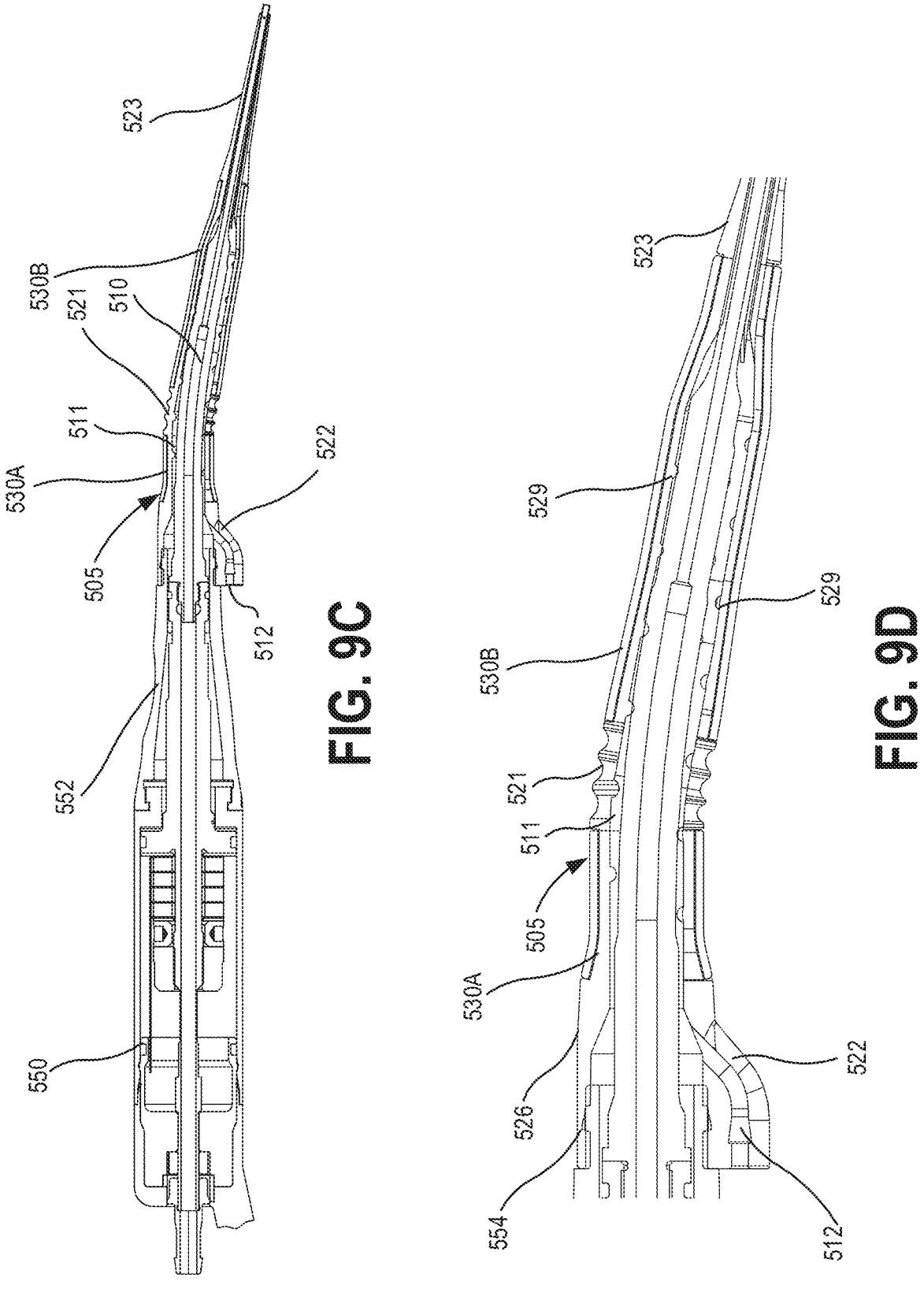

As shown in FIG. 9C, the sheath assembly defines a first channel 511 around the probe 510. The first channel 511 is configured to convey fluid to a distal tip of the probe 510. In some embodiments, the proximal end of the deformable sheath may define a second channel 512 configured to be coupled to a fluid supply and communicate the fluid from the fluid supply to the first channel 511.

As shown in FIG. 9D, the first rigid sheath 530A may be configured to abut a surface of a proximal ridge of the deformable section 521, and the second rigid sheath 530B may be configured to abut a surface of a distal ridge of the deformable section 521 such that the first rigid sheath 530A and the second rigid sheath 530B are secured in position relative to the deformable sheath. In some embodiments, the rigid sheath(s) 530A, 530B may enclose about 80%, about 90%, about 95% of the length of the deformable sheath. The deformable sheath may include a plurality of protrusions 529 configured to space the deformable sheath from the probe 510 such that the deformable sheath defines a channel around the probe for fluid to flow. The sheath assembly 505 may be structurally and/or functionally similar to the sheath assembly 105, and therefore, certain details of the sheath assembly 505 are not described herein with respect to FIGS. 8A-9D.

Figure 10A:
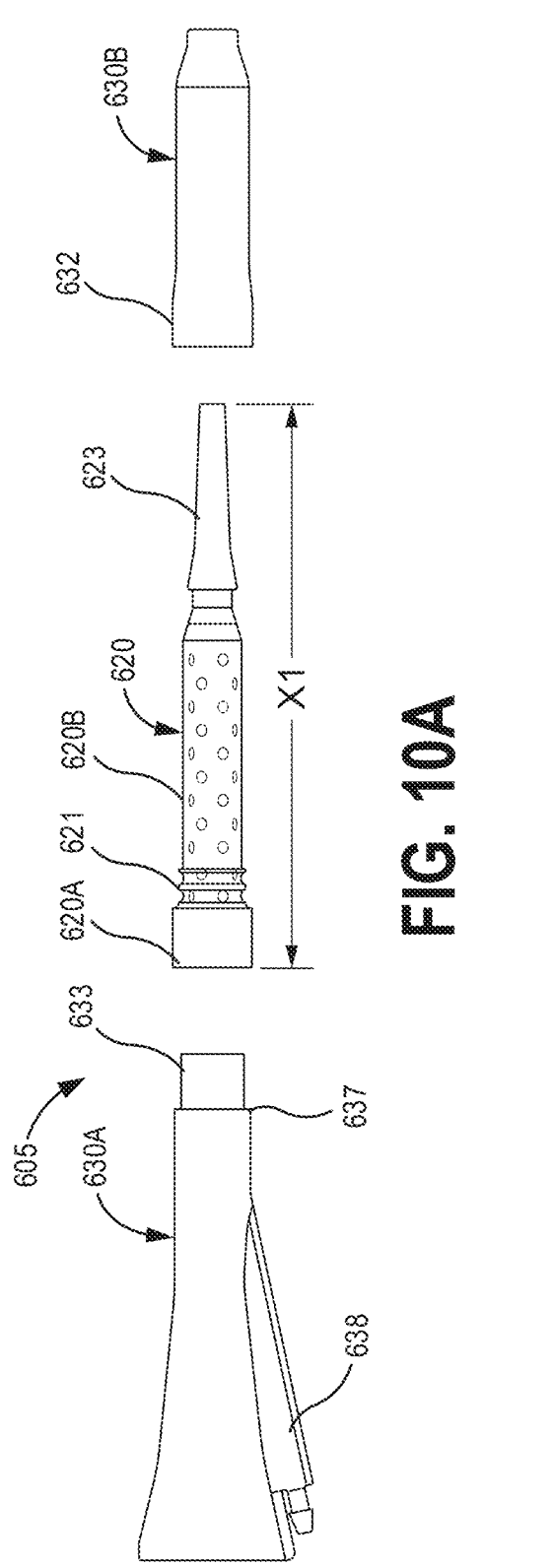
FIGS. 10A-10B show a sheath assembly for an ultrasonic probe in an unassembled and assembled configuration, respectively, according to embodiments.
Figure 10B:
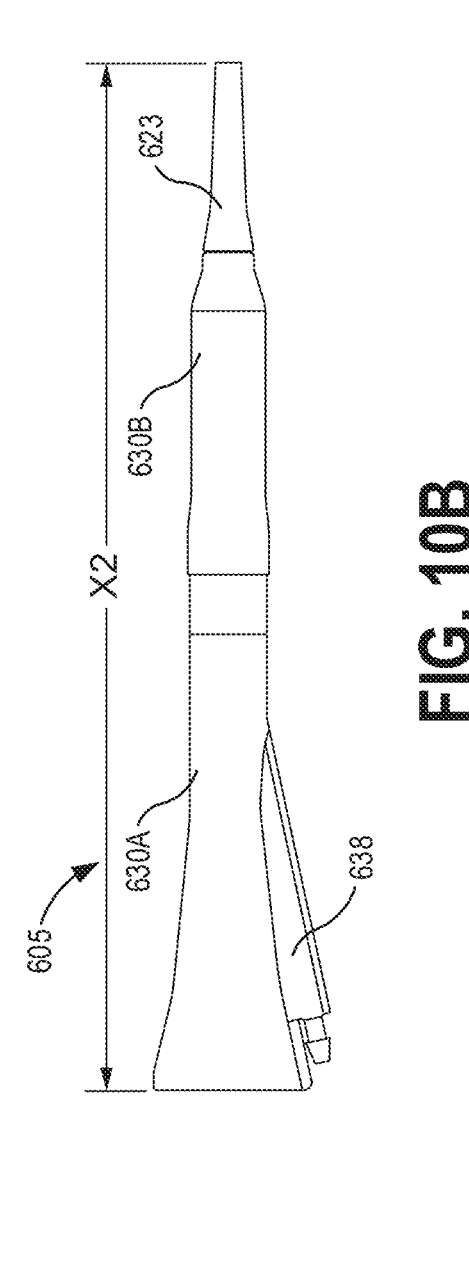

FIGS. 10A-10B show a sheath assembly 605 for an ultrasonic probe in an unassembled and assembled configuration, respectively. The sheath assembly 605 can include a deformable sheath 620 including a proximal portion 620A and a distal portion 620B with a deformable section 621 therebetween. The deformable sheath 620 may further include a distal tip 623 configured to align with a distal end of the probe when the deformable sheath 620 is disposed around the probe. At least a portion of the deformable sheath 620 (e.g., the distal portion 620B) may include one or more protrusions configured to maintain a space between the probe and an inner surface of the deformable sheath for fluid flow. The deformable section 621 may include a bellowed section (e.g., accordion-like, corrugated, etc.) configured to bend up to a predetermined angle. In some embodiments, the deformable section 621 may be configured to bend omni-directionally.

Figure 11A:
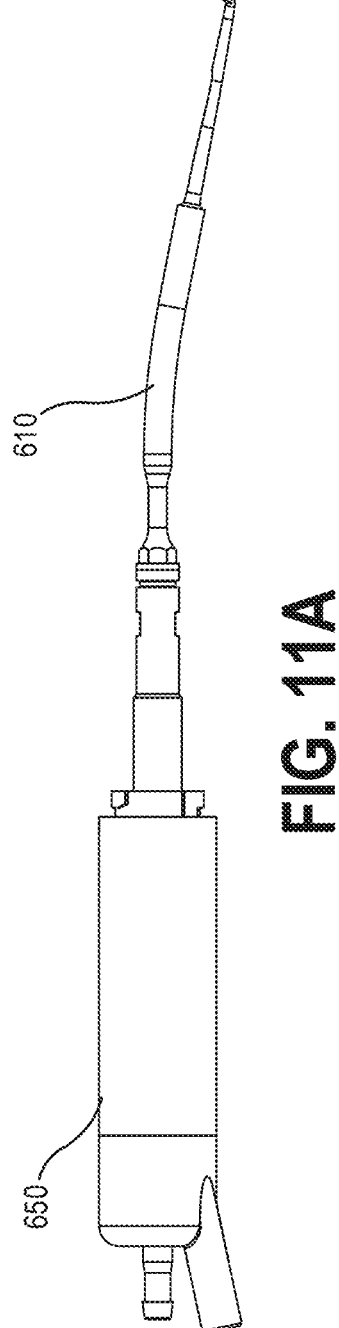
FIGS. 11A-11D show different views of the ultrasonic probe and sheath assembly of FIGS. 10A-10B.
Figure 11B:
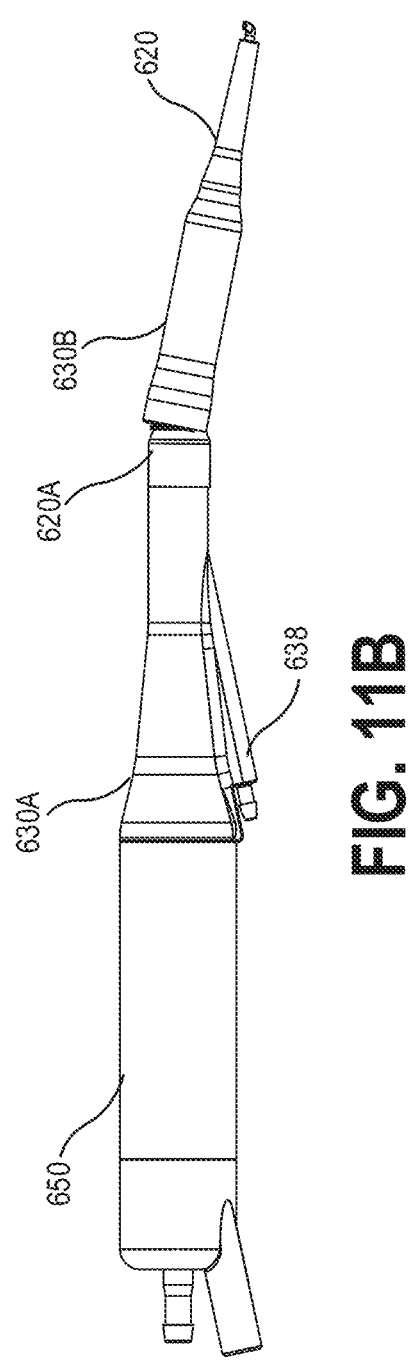

The sheath assembly 605 further includes a first rigid sheath 630A configured to be coupled to a first end portion (e.g., the proximal end 620A) of the deformable sheath 620. The first rigid sheath 630A may have a distal portion 633 configured to be disposed within the proximal end 620A of the deformable sheath 620. For example, the proximal end 620A of the deformable sheath 620 may be configured to fit over a distal end portion 633 of the first rigid sheath 630A. Therefore, the deformable sheath 620 may be disposed around a distal portion of the probe while the first rigid sheath 630A is disposed around a proximal portion of the probe. In some embodiments, the distal end portion 633 of the first rigid sheath 630A may include a form-locking feature configured to prevent accidental decoupling of the first rigid sheath 630A and the deformable sheath. For example, the form-locking feature may prevent the deformable sheath from slipping off the distal end portion 633 of the first rigid sheath 630A. In some embodiments, the first rigid sheath 630A may define a surface feature or ledge 637 a predetermined distance from a distal end of the first rigid sheath 630A such that when the first rigid sheath 630A is disposed under the deformable sheath 620, the distal end of the first rigid sheath 630A aligns with a proximal end of the deformable section 621. In other words, the surface feature of the first rigid sheath 630A may space the rigid sheath 630A from the deformable section 621. The sheath assembly 605 may further include a second rigid sheath 630B configured to be disposed around a second end portion 620B of the deformable sheath 620. The second rigid sheath 630B may be disposed on a distal side of the deformable section 621. In some embodiments, the distal portion 620B of the deformable sheath 620 may include a pair of surface features configured to align the second rigid sheath 630B relative to the first rigid sheath 630A such that that the first rigid sheath 630A and second rigid sheath 630B enclose at least a portion of the deformable section 621 while defining a gap therebetween such that the deformable sheath 620 can bend. In some embodiments, the second rigid sheath 630B includes an enlarged section 632 configured to be disposed over the deformable section 621 when the second rigid sheath 630B is coupled to the deformable sheath 620. The enlarged section may have increased diameter and/or outer diameter to provide space for the deformable sheath and probe to curve while providing protection around the deformable sheath and probe, as shown in FIG. 11B. The second rigid sheath 630B may further include a tapered distal end. The tapered distal end may taper according to ta taper of the deformable sheath 620 and/or the probe.

As shown in FIG. 10B, the first rigid sheath 630A and second rigid sheath 630B may enclose a main body of the probe (aside from the distal tip and a portion of the deformable section 621) to prevent the user from contacting or applying pressure to the probe. Therefore, the rigid sheaths 630A, 630B may prevent ultrasonic vibrations from transferring to the user when the user holds the sheath assembly

605. In some embodiments, sheath assembly 605 may define a channel around the probe to convey fluid to the distal tip of the probe. In some embodiments, the first rigid sheath 630A may define a port or second channel 638 configured to deliver fluid to the first channel.

In some embodiments, the deformable sheath 620 may have a first length X1, and the sheath assembly may have a second length X2 larger than the first length X1. In some embodiments, the second length X2 may correspond to a total length of the probe (see, for example, FIG. 9D).

Figures 11C, 11D:
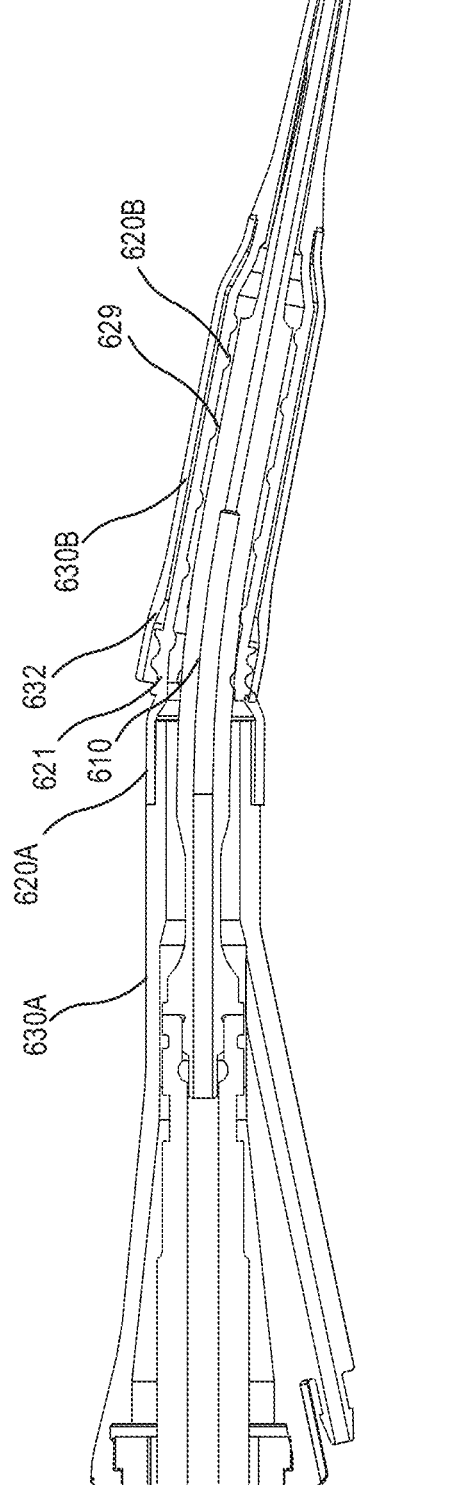
Figures 12A, 12B:
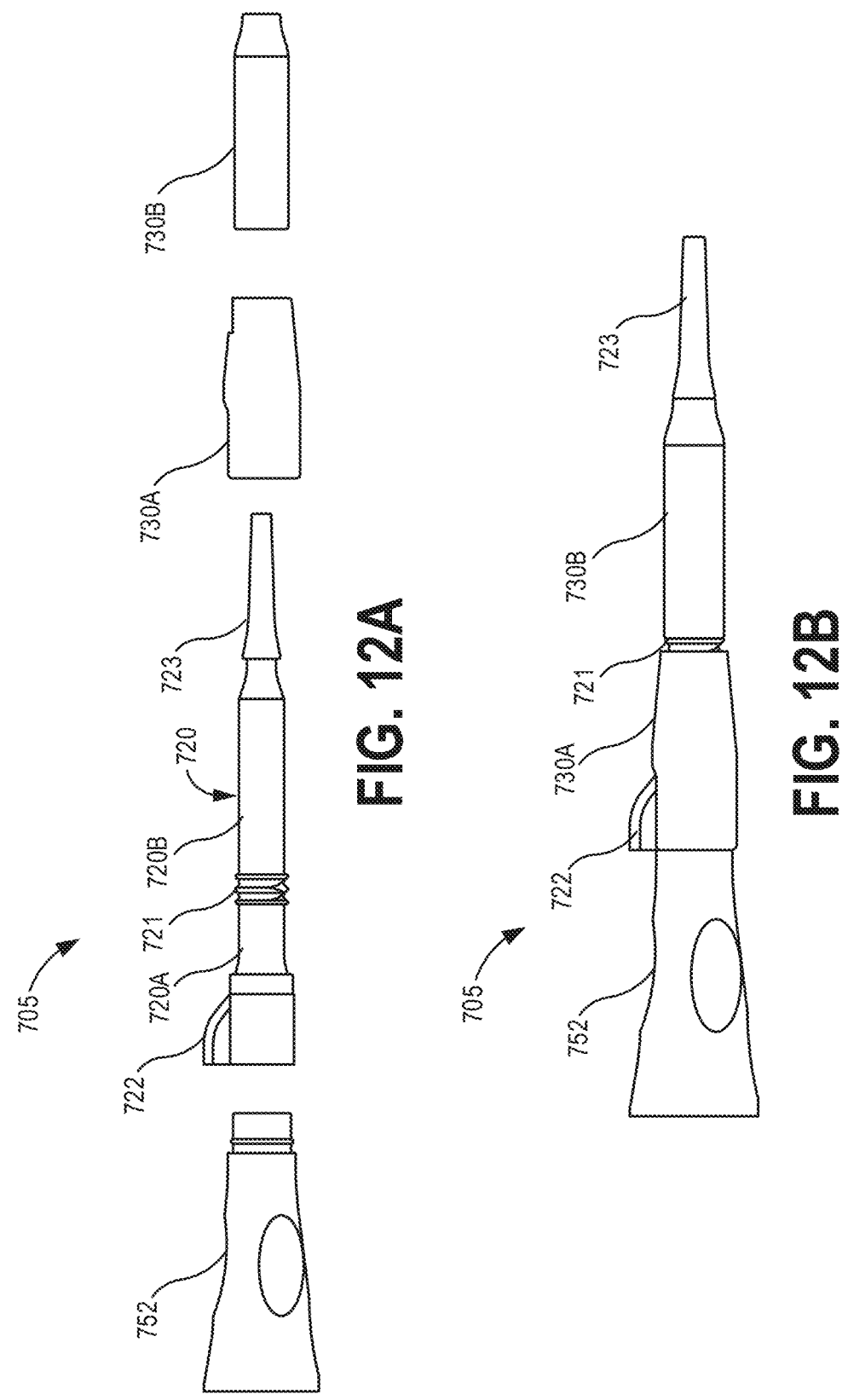
FIGS. 12A-12B show a sheath assembly for an ultrasonic probe in an unassembled and assembled configuration, respectively, according to embodiments.

FIG. 11D shows a close up of an engagement between the first rigid sheath 630A and a proximal end 620A of the deformable sheath 620 and an alignment of the enlarged section 632 of the second rigid sheath 630B over the deformable section 621. Therefore, the sheath assembly 605 can curve or bend while being protected by rigid material at the joint. As shown, the gap between the first rigid section 630A and the second rigid section 630B is sufficiently small such that a user could not apply pressure to the deformable sheath, and therefore, the probe 610. The distal portion 620B of the deformable sheath includes a plurality of protrusions 629 configured to space the deformable sheath from the probe.

FIGS. 12A-13B show a sheath assembly 705 for an ultrasonic probe in an unassembled and assembled configuration, respectively, according to embodiments. In some embodiments, the sheath assembly 705 can include a deformable sheath 721 including a proximal portion 720A and a distal portion 720B with a deformable section 721 therebetween. The proximal portion 720A can be configured to be coupled to a connector 752 (and the handle, not shown). The proximal portion 720A can include a lip or ridge 722 and/or defining a channel configured to be coupled to a fluid supply. The lip or ridge 722 may similar to the lip or ridge 322, 422, 522, 622. The deformable section 721 can include a bellowed section configured to deform or bend according to a geometry of the probe. The bellowed section may be configured to bend omnidirectionally up to a predetermined angle from the longitudinal axis. The deformable sheath 720 may further include a distal tip 723 configured to align with a distal end of the probe. The distal tip 723 of the deformable sheath 720 may taper according to a taper of the distal end of the probe. The sheath assembly 705 can further include a first rigid sheath 730A configured to be disposed around the proximal portion 720A of the deformable sheath. The sheath assembly 705 may further include a second rigid sheath 730B configured to be disposed around a distal portion 720B of the deformable sheath 720. In some embodiments, when the first rigid sheath 730A and the second rigid sheath 730B are coupled to the deformable sheath, the first rigid sheath 730A and the second rigid sheath 730B may define a gap therebetween such that the deformable sheath can deform or bend. However, the gap may be sufficiently small such that the user cannot press the deformable sheath 720 against the probe and/or apply pressure to the probe.

Figures 13A, 13B:
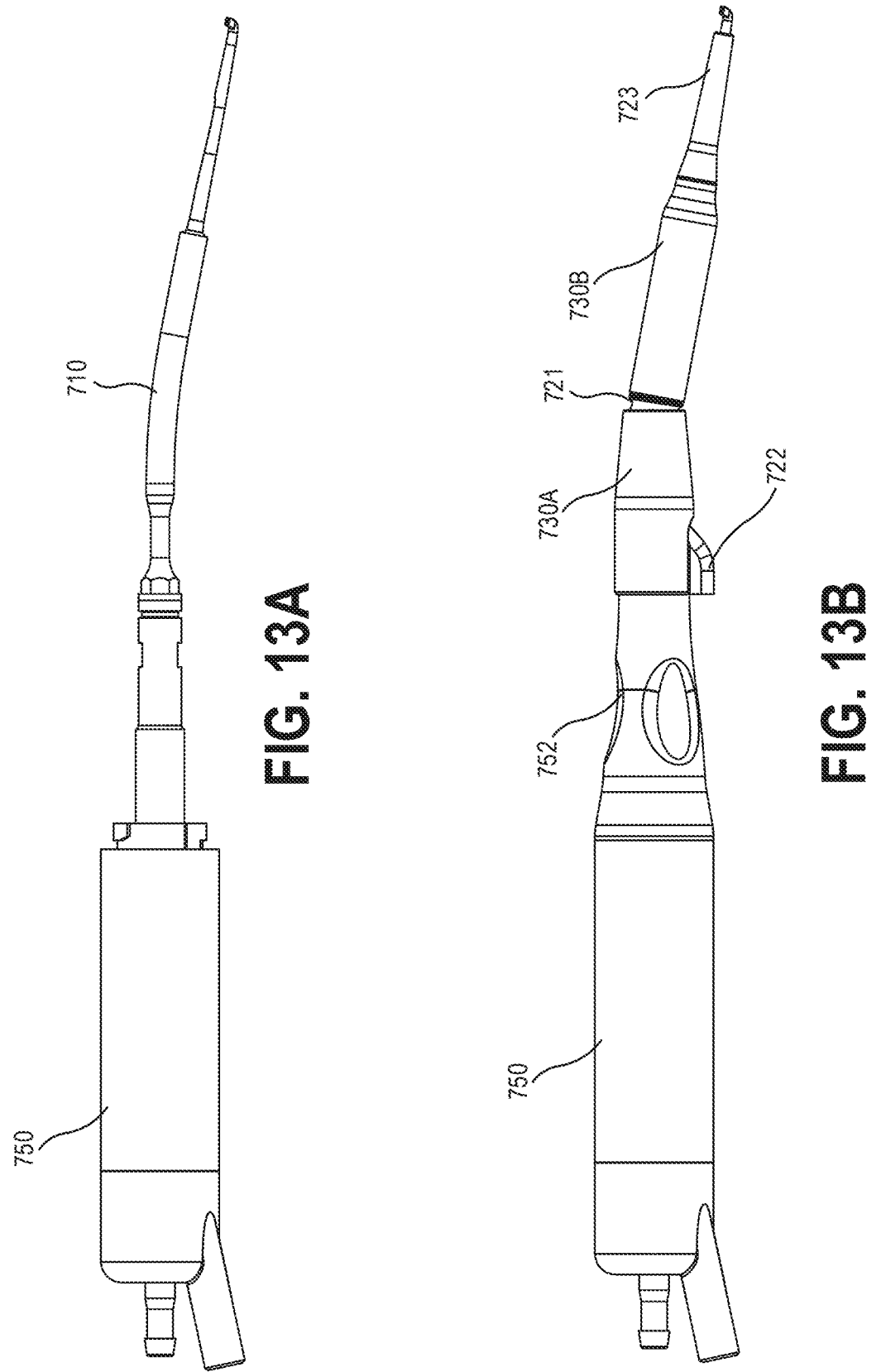
FIGS. 13A-13D show different views of the ultrasonic probe and sheath assembly of FIGS. 12A-12B.
Figures 13C, 13D:
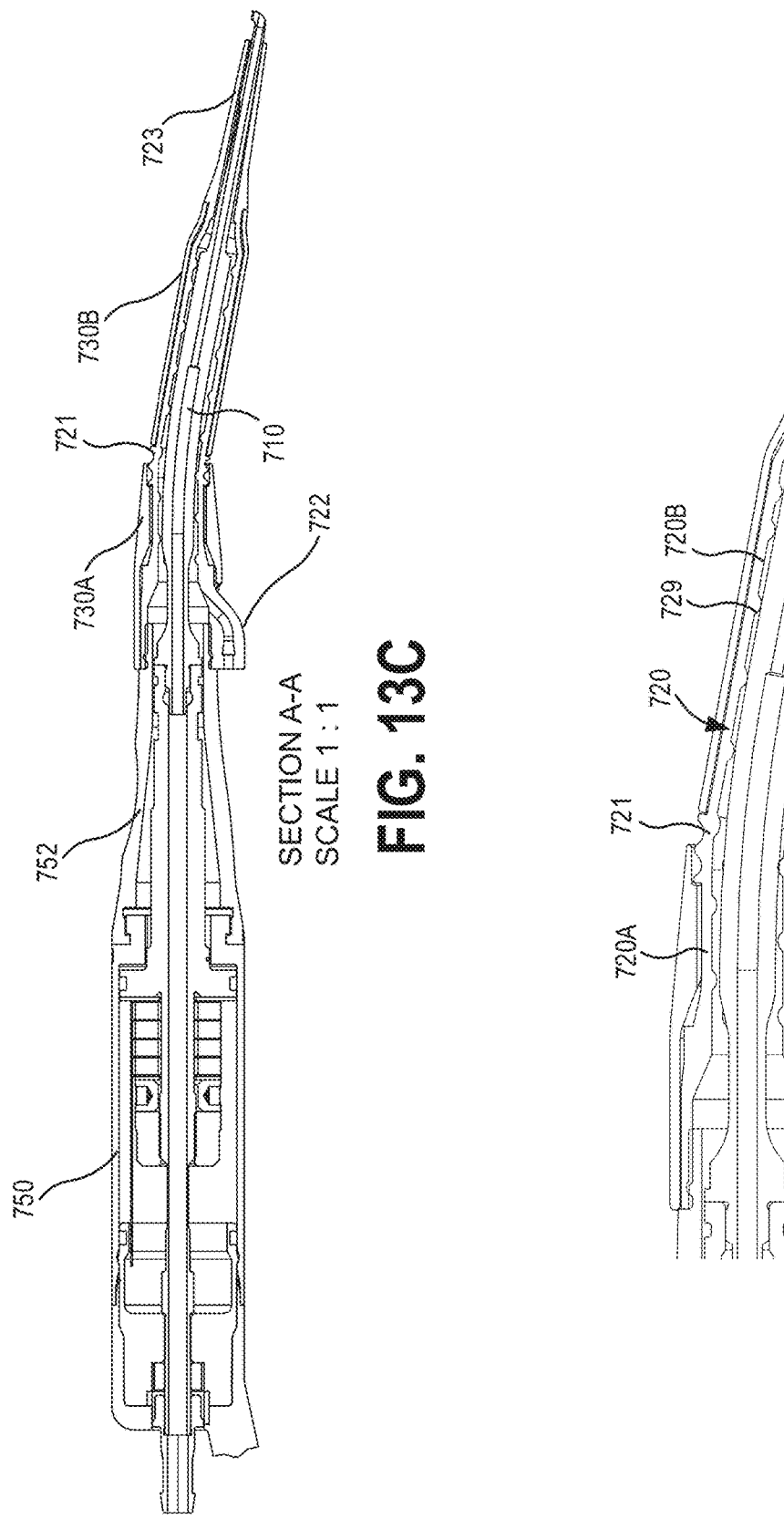

As shown in FIGS. 13C-13D, the deformable section 721 may include one or more surface features configured to align the first rigid sheath 730A and the second rigid sheath 730B relative to the deformable section 721 and relative to each other. In some embodiments, the first rigid sheath 730A may be configured to abut a proximal ridge of the deformable section 721. In some embodiments, the second rigid sheath 730B may be configured to abut a distal ridge of the deformable section 721. In some embodiments, the first rigid sheath 730A may include a ledge or overhang at a distal end configured to extend over a portion of the deformable section 721 to enclose the portion of the deformable section 721 and reduce an amount of the deformable section 721 that is exposed.

As shown in FIGS. 13C-13D, the deformable sheath 720 maintains a spacing from an outer surface of the probe such that fluid can flow to the distal tip of the probe 710. The deformable sheath 720 includes a plurality of protrusions 729 on an inner surface thereof to maintain the deformable sheath 720 at a predetermined distance from the probe 710. Therefore, the deformable sheath 720 defines a first channel around the probe. The proximal end of the deformable sheath 720 may define a second channel 712 configured to be coupled to a fluid supply.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications and anatomy (e.g., intracranial and extracranial vascular structure) for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The specific examples and descriptions herein are exemplary in nature and embodiments may be developed by those skilled in the art based on the material taught herein without departing from the scope of the present invention.

The invention claimed is:

1. An apparatus, comprising:
   a deformable sheath disposable around an ultrasonic probe including a curved section, the deformable sheath including a deformable section configured to deform according to the curved section of the ultrasonic probe;
   a first rigid section coupleable to the deformable sheath on a first side of the deformable section; and
   a second rigid section coupleable to the deformable sheath on a second side of the deformable section,
   the first rigid section and the second rigid section when coupled to the deformable sheath defining a gap therebetween such that the deformable section can deform up to a predetermined angle from a longitudinal axis of a proximal portion of the deformable sheath, at least one of the first rigid section or the second rigid section including an enlarged section configured to be disposed around the deformable section such that the deformable section deforms within the enlarged section,
   the first rigid section and the second rigid section configured to maintain a separation between the ultrasonic probe and an inner surface of the first rigid section and the second rigid section to reduce transfer of ultrasonic vibrations generated by the ultrasonic probe through the first rigid section and the second rigid section to a user grasping the first rigid section or the second rigid section.

2. The apparatus of claim 1, wherein the deformable section is a bellowed section configured to bend according to a curvature of the curved section of the ultrasonic probe when the deformable sheath is disposed around the ultrasonic probe.

3. The apparatus of claim 1, wherein the first rigid section is configured to be disposed around the proximal portion of the deformable sheath, and the second rigid section is configured to be disposed around a distal portion of the deformable sheath.

4. The apparatus of claim 1, wherein a distal portion of the first rigid section is configured to be disposed within the proximal portion of the deformable sheath, and the second rigid section is configured to be disposed around a distal portion of the deformable sheath.

5. The apparatus of claim 1, wherein the deformable sheath includes one or more surface features, at least one of the first rigid section or the second rigid section disposable around the deformable sheath in engagement with the one or more surface features.

6. The apparatus of claim 5, wherein the one or more surface features are configured to align at least one of the first rigid section or the second rigid section relative to the deformable section.

7. The apparatus of claim 1, wherein the deformable sheath includes one or more protrusions configured to define a spacing between an inner surface of the deformable sheath and an outer surface of the ultrasonic probe, the spacing being configured to allow delivery of a fluid to a distal end of the ultrasonic probe.

8. The apparatus of claim 1, wherein an outer surface of at least one of the first rigid section or the second rigid section forms a seamless surface with neighboring sections of the deformable sheath when at least one of the first rigid section or the second rigid section are coupled to the deformable sheath.

9. The apparatus of claim 1, wherein the predetermined angle is 20 degrees.

10. An apparatus, comprising:

a deformable sheath disposable around an ultrasonic probe including a curved section, the deformable sheath including a deformable section configured to deform according to the curved section of the ultrasonic probe, wherein the deformable section is a bellowed section configured to deform according to a curvature of the curved section of the ultrasonic probe when the deformable sheath is disposed around the ultrasonic probe;

a first rigid section configured to be disposed around the deformable sheath on a first side of the deformable section; and a second rigid section configured to be disposed around the deformable sheath on a second side of the deform-able section, the deformable sheath including at least one surface feature on an outer surface thereof, the at least one surface feature configured to engage the first rigid section to align the first rigid section relative to the second rigid section and the deformable section.

11. The apparatus of claim 10, wherein the at least one surface feature includes a first surface feature configured to engage the first rigid section and a second surface feature configured to engage the second rigid section, the first surface feature and the second surface feature configured to space the first rigid section and the second rigid section such that the deformable section can deform according to the curved section of the ultrasonic probe.

12. The apparatus of claim 10, wherein the deformable sheath includes one or more protrusions configured to define a spacing between an inner surface of the deformable sheath and an outer surface of the ultrasonic probe, the spacing being configured to allow delivery of a fluid to a distal end of the ultrasonic probe.

13. The apparatus of claim 10, wherein an outer surface of at least one of the first rigid section or the second rigid section forms a seamless surface with neighboring sections of the deformable sheath when the at least one of the first rigid section or the second rigid section are coupled to the deformable sheath.

14. The apparatus of claim 10, wherein the deformable section is configured to deform relative to a longitudinal axis of a proximal section of the deformable sheath up to about 20 degrees.

15. An apparatus, comprising:

a deformable sheath disposable around an ultrasonic probe including a curved section, the deformable sheath including a deformable section configured to deform according to the curved section of the ultrasonic probe, the deformable sheath includes one or more protrusions configured to define a spacing between an inner surface of the deformable sheath and an outer surface of the ultrasonic probe, the spacing being configured to allow delivery of a fluid to a distal end of the ultrasonic probe;

a first rigid section configured to be disposed around the deformable sheath on a first side of the deformable section; and a second rigid section configured to be disposed around the deformable sheath on a second side of the deform-able section, the deformable sheath further including at least one surface feature on an outer surface thereof, the at least one surface feature configured to engage the first rigid section to align the first rigid section relative to the second rigid section and the deformable section.

16. The apparatus of claim 15, wherein the first rigid section includes an enlarged section configured to align with the deformable section such that the deformable section can deform within the enlarged section.

17. The apparatus of claim 15, wherein the deformable section of the deformable sheath is configured to bend omnidirectionally.

18. The apparatus of claim 15, wherein the deformable section is a bellowed section configured to bend according to a curvature of the curved section of the ultrasonic probe when the deformable sheath is disposed around the ultra-sonic probe.

19. The apparatus of claim 15, wherein an outer surface of at least one of the first rigid section or the second rigid section forms a seamless surface with neighboring sections of the deformable sheath when the at least one of the first rigid section or the second rigid section are coupled to the deformable sheath.

20. The apparatus of claim 15, wherein the deformable section is configured to deform relative to a longitudinal axis of a proximal section of the deformable sheath up to about 20 degrees.

21. The apparatus of claim 15, wherein the first rigid section and second rigid section are configured to maintain a separation between the ultrasonic probe and an inner surface of the first rigid section and the second rigid section to reduce transfer of ultrasonic vibrations generated by the ultrasonic probe through the first rigid section and the second rigid section to a user grasping the first rigid section or the second rigid section.

22. An apparatus, comprising:

a deformable sheath disposable around an ultrasonic probe including a curved section, the deformable sheath including a deformable section configured to deform according to the curved section of the ultrasonic probe;

a first rigid section configured to be disposed around the deformable sheath on a first side of the deformable section; and a second rigid section configured to be disposed around the deformable sheath on a second side of the deform-able section, the deformable sheath further including at least one surface feature on an outer surface thereof, the at least one surface feature configured to engage the first rigid section to align the first rigid section relative to the second rigid section and the deformable section, the outer surface of at least one of the first rigid section or the second rigid section forms a seamless surface with neighboring sections of the deformable sheath when the at least one of the first rigid section or the second rigid section are coupled to the deformable sheath.

23. The apparatus of claim 22, wherein the first rigid section includes an enlarged section configured to align with the deformable section such that the deformable section can deform within the enlarged section.

24. The apparatus of claim 22, wherein the deformable section is a bellowed section configured to bend according to a curvature of the ultrasonic probe when the deformable sheath is disposed around the ultrasonic probe.

25. The apparatus of claim 22, wherein the first rigid section and second rigid section are configured to maintain a separation between the ultrasonic probe and an inner surface of the first rigid section and the second rigid section to reduce transfer of ultrasonic vibrations generated by the ultrasonic probe through the first rigid section and the second rigid section to a user grasping the first rigid section or the second rigid section.

26. The apparatus of claim 22, wherein the first rigid section and the second rigid section when coupled to the deformable sheath defining a gap therebetween such that the deformable section can deform up to a predetermined angle from a longitudinal axis of a proximal portion of the deformable sheath.

27. The apparatus of claim 26, wherein the predetermined angle is 20 degrees.

\* \* \* \* \*